(12) United States Patent
Suga et al.

(10) Patent No.: US 10,869,640 B2
(45) Date of Patent: Dec. 22, 2020

(54) OPERATION TABLE WITH ROBOT ARM

(71) Applicant: Medicaroid Corporation, Kobe (JP)

(72) Inventors: Kazunori Suga, Kobe (JP); Tetsuya Nakanishi, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 597 days.

(21) Appl. No.: 15/722,161

(22) Filed: Oct. 2, 2017

(65) Prior Publication Data
US 2018/0110486 A1  Apr. 26, 2018

(30) Foreign Application Priority Data

Oct. 26, 2016  (JP) ................................ 2016-209902

(51) Int. Cl.
| | |
|---|---|
| *A61B 6/04* | (2006.01) |
| *A61G 13/04* | (2006.01) |
| *A61G 13/06* | (2006.01) |
| *A61B 34/00* | (2016.01) |
| *A61G 13/02* | (2006.01) |
| *A61G 13/10* | (2006.01) |
| *A61G 13/00* | (2006.01) |

(52) U.S. Cl.
CPC ............ *A61B 6/0487* (2020.08); *A61B 34/71* (2016.02); *A61G 13/02* (2013.01); *A61G 13/04* (2013.01); *A61G 13/06* (2013.01); *A61G 13/10* (2013.01); *A61G 13/0018* (2013.01); *A61G 2210/50* (2013.01)

(58) Field of Classification Search
CPC ...... A61B 6/0457; A61B 34/71; A61G 13/02; A61G 13/04; A61G 13/06; A61G 13/08; A61G 13/10; A61G 13/0018; A61G 2210/50
See application file for complete search history.

(56) References Cited

U.S. PATENT DOCUMENTS

| | | | | |
|---|---|---|---|---|
| 5,149,074 A | * | 9/1992 | Jarin ...................... | A61B 6/04 5/601 |
| 5,744,728 A | * | 4/1998 | Suita ...................... | B25J 19/063 73/862.542 |
| 6,502,261 B1 | * | 1/2003 | Harwood .............. | A61B 6/0457 108/145 |

(Continued)

FOREIGN PATENT DOCUMENTS

| | | |
|---|---|---|
| JP | H11-509461 A | 8/1999 |
| JP | 2008-539963 A | 11/2008 |

(Continued)

*Primary Examiner* — Robert G Santos
*Assistant Examiner* — Rahib T Zaman
(74) *Attorney, Agent, or Firm* — Metrolex IP Law Group, PLLC

(57) ABSTRACT

One or more embodiments of an operation table may include a table on which a patient is to be placed; a base fixed on a floor; and a robot arm comprising joints, a first end supported by the base, and a second end supporting the table, wherein the robot arm takes a first posture in which the robot arm is stored in a storage space that is a space under the table when the table is positioned at a first position, and the robot arm moves the table to a second position which is away from the first position by taking a second posture in which at least part of the robot arm horizontally protrudes from the storage space.

20 Claims, 18 Drawing Sheets

(56) References Cited

U.S. PATENT DOCUMENTS

| | | | | |
|---|---|---|---|---|
| 7,860,550 | B2* | 12/2010 | Saracen | A61N 5/1049 600/410 |
| 8,126,114 | B2* | 2/2012 | Naylor | A61B 34/30 378/65 |
| 8,160,205 | B2 | 4/2012 | Saracen et al. | |
| 8,359,982 | B2* | 1/2013 | Lebel | A47B 23/043 108/44 |
| 8,740,880 | B2* | 6/2014 | Pinault | A61N 5/1049 606/1 |
| 9,326,907 | B2* | 5/2016 | Marle | A61G 7/1057 |
| 2005/0234327 | A1* | 10/2005 | Saracen | A61B 6/548 600/407 |
| 2015/0000038 | A1* | 1/2015 | Obi | A61B 6/0407 5/601 |
| 2015/0059095 | A1* | 3/2015 | Bergfjord | A61N 5/1069 5/611 |

FOREIGN PATENT DOCUMENTS

| | | |
|---|---|---|
| JP | 2009-131718 A | 6/2009 |
| JP | 2013-126454 A | 6/2013 |

\* cited by examiner

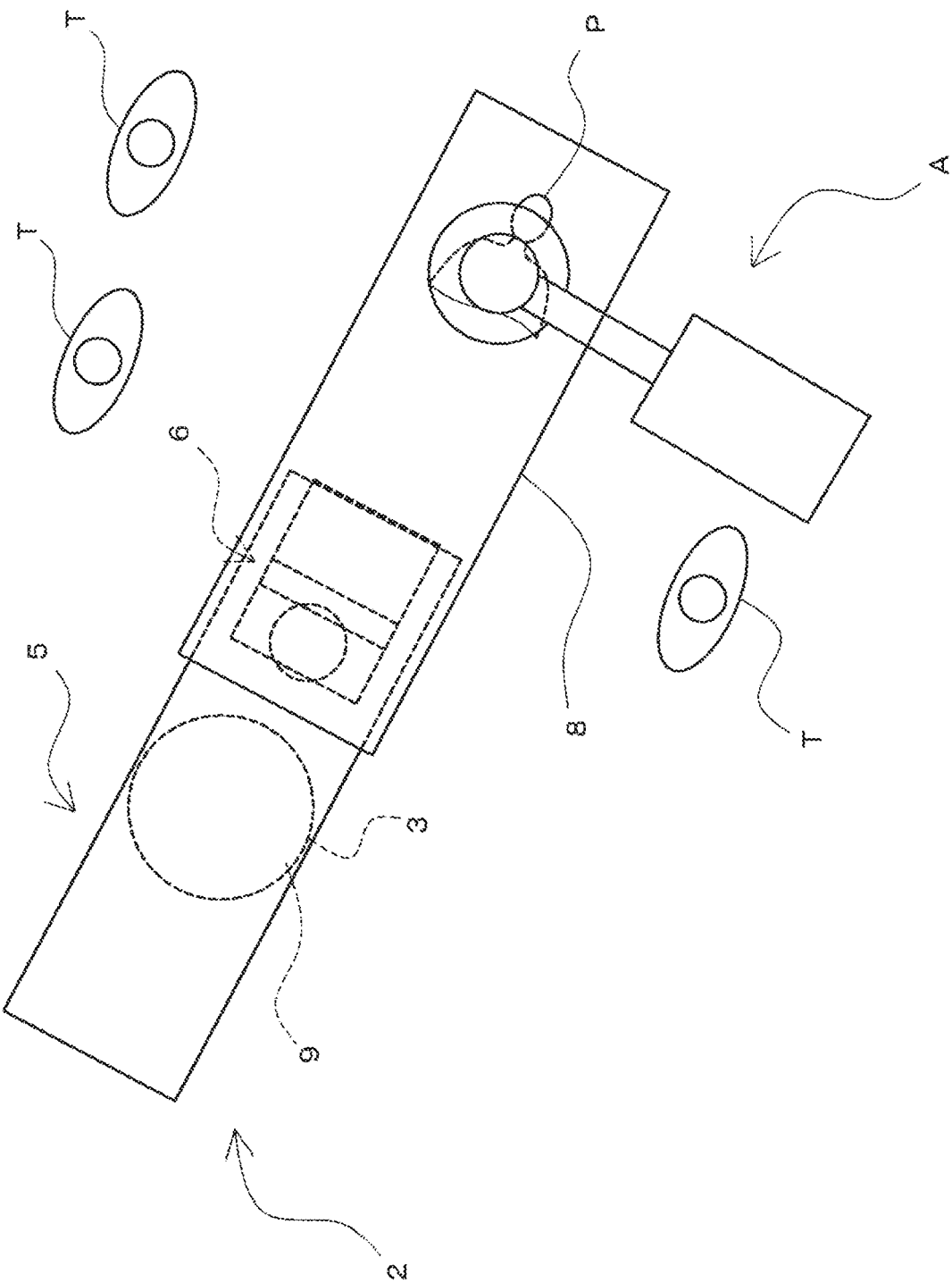

OPERATION TABLE WITH ROBOT ARM

CROSS REFERENCE TO RELATED APPLICATIONS

This application claims priority based on 35 USC 119 from prior Japanese Patent Application No. 2016-209902 filed on Oct. 26, 2016, entitled "OPERATION TABLE WITH ROBOT ARM", the entire contents of which are incorporated herein by reference.

BACKGROUND

The present disclosure relates to a robotic operation table equipped with a robot arm that moves a table on which a patient is placed.

It has been recognized that operation results are improved by preoperative and intraoperative imaging using radiographic X-ray equipment in a hybrid operating room. For instance, operation table 2 disclosed by Japanese Unexamined Patent Application Publication No. 2013-126454 (Patent Literature 1, corresponding to U. S. Patent Application No. 2015/0000038) is provided with caster 6. For induction of anesthesia, an operation, X-ray photography and others, a medical worker moves operation table 2 by pushing operation table 2.

However, with this operation table, it is necessary, when moving the operation table, to pay careful attention to the condition and safety of a patient while keeping in mind interference with various peripheral devices used for an operation and the piping and cables of the various peripheral devices. Also, a human error sometimes occurs in which after the movement, a medical worker forgets to apply a brake to prevent the operation table from being moved.

Regarding this point, Japanese National Publication of International Patent Application No. 2008-539963 (Patent Literature 2, corresponding to U.S. Pat. No. 8,160,205) and Japanese Unexamined Patent Application Publication No. 2009-131718 (Patent Literature 3, corresponding to U.S. Pat. No. 7,860,550) describe techniques related to a radiation for treatment management system that moves a table, on which a patient is placed, by a robot arm. When the technique is applied to an operation table, the above-mentioned problem, which occurs when the operation table is moved, can be eliminated.

SUMMARY

One or more embodiments of an operation table may comprise a table on which a patient is to be placed; a base fixed on a floor; and a robot arm comprising joints, a first end supported by the base, and a second end supporting the table, wherein the robot arm takes a first posture in which the robot arm is stored in a storage space that is a space under the table when the table is positioned at a first position, and the robot arm moves the table to a second position which is away from the first position by taking a second posture in which at least part of the robot arm horizontally protrudes from the storage space.

One or more embodiments of an operation table may comprise a table on which a patient is to be placed; a base fixed on a floor; and a robot arm comprising at least six joints, a first end supported by the base, and a second end supporting the table, wherein the table is positioned at a predetermined position, and the robot arm takes a posture in which a length of the robot arm in a longitudinal direction of the table is less than or equal to a length of the table in the longitudinal direction, and a length of the robot arm in a widthwise direction of the table is less than or equal to a length of the table in the widthwise direction.

One or more embodiments of a method of transferring a patient may comprise positioning a table at a first position by a robot arm of an operation table, wherein the operation table comprises the table on which a patient is to be placed, a base fixed on a floor, and the robot arm comprising at least six joints, a first end supported by the base and a second end supporting the table, wherein when the table is positioned at the first position, the robot arm takes a first posture in which the robot arm is stored in a storage space that is a space under the table; and moving the table to a second position different from the first position by the robot arm, wherein when the table is positioned at the second position, the robot arm takes a second posture in which at least part of the robot arm horizontally protrudes from the storage space.

BRIEF DESCRIPTION OF DRAWINGS

FIG. 7 is a schematic view of an operating room, in which a robotic operation table is set, as seen from above, and the view illustrates a state of a patient transported to a test position;

DETAILED DESCRIPTION

Figure 1:
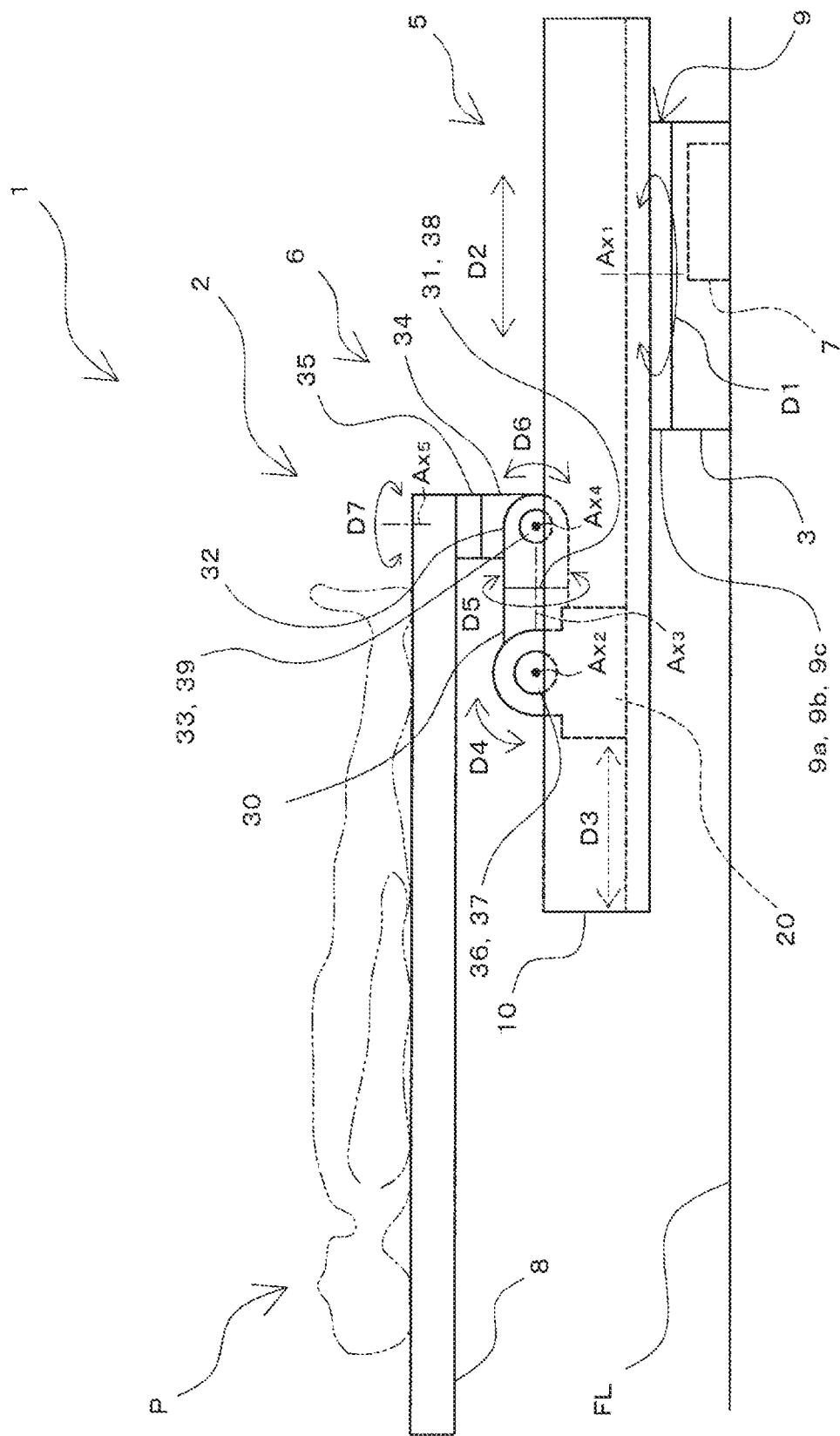
FIG. 1 is a side view schematically illustrating a robotic operation table according to a first implementation.

Embodiments are explained with reference to drawings. In the respective drawings referenced herein, the same constituents are designated by the same reference numerals and duplicate explanation concerning the same constituents is basically omitted. All of the drawings are provided to illustrate the respective examples only. No dimensional proportions in the drawings shall impose a restriction on one or more embodiments. For this reason, specific dimensions and the like should be interpreted with the following descriptions taken into consideration. In addition, the drawings may include parts whose dimensional relationship and ratios are different from one drawing to another.

In medical practice, in various situations, improvement of medical practice is being pursued for efficient and highly accurate treatment, test, and measurement while maintaining the safety. In an implementation, it is proposed to promote these by introducing a robotic operation table supported by a robot arm having multiple degrees of freedom to medical practice to replace a conventional operation table.

The robotic operation table according to the following implementations may be used when a hybrid operation is performed in which for instance, capturing an image using radiographic X-ray equipment and an operation according to a resultant image are performed in the same room. Hereinafter, a description is given by taking an example in which a robotic operation table is used for the above-described hybrid operation.

(First Implementation)

FIG. 1 is a side view of robotic operation table 1 according to a first implementation. Robotic operation table 1 includes robot arm 2, base 3, and table 8. In robotic operation table 1, one end of robot arm 2 having multiple degrees (six degrees of freedom in the case of the first implementation) of freedom is supported rotatably about a vertical axis by base 3, whereas the other end of robot arm 2 supports table 8 for placing patient P. As table 8 used in the first implementation, for instance, a table with a length dimension of 2100 mm and a width dimension of 500 mm is used as an example. It is to be noted that the degrees of freedom of the robot arm in this implementation and the implementations described below also include a rotational degree of freedom between the robot arm and the base.

It is to be noted that hereinafter, roll axis is defined as an axis extending in a direction parallel to the longitudinal direction of table 8, pitch axis is defined as an axis extending in a direction parallel to the widthwise direction of table 8, and yaw axis is defined as an axis perpendicular to both the roll axis and the pitch axis.

Base 3 is a base section fixed to floor FL. The inside of base 3 is provided with control device 7 described later in detail. It is to be noted that base 3 may be embedded in the floor.

Robot arm 2 includes base-side movable part 9, linear movement assembly 5, and wrist assembly 6.

Figure 2:
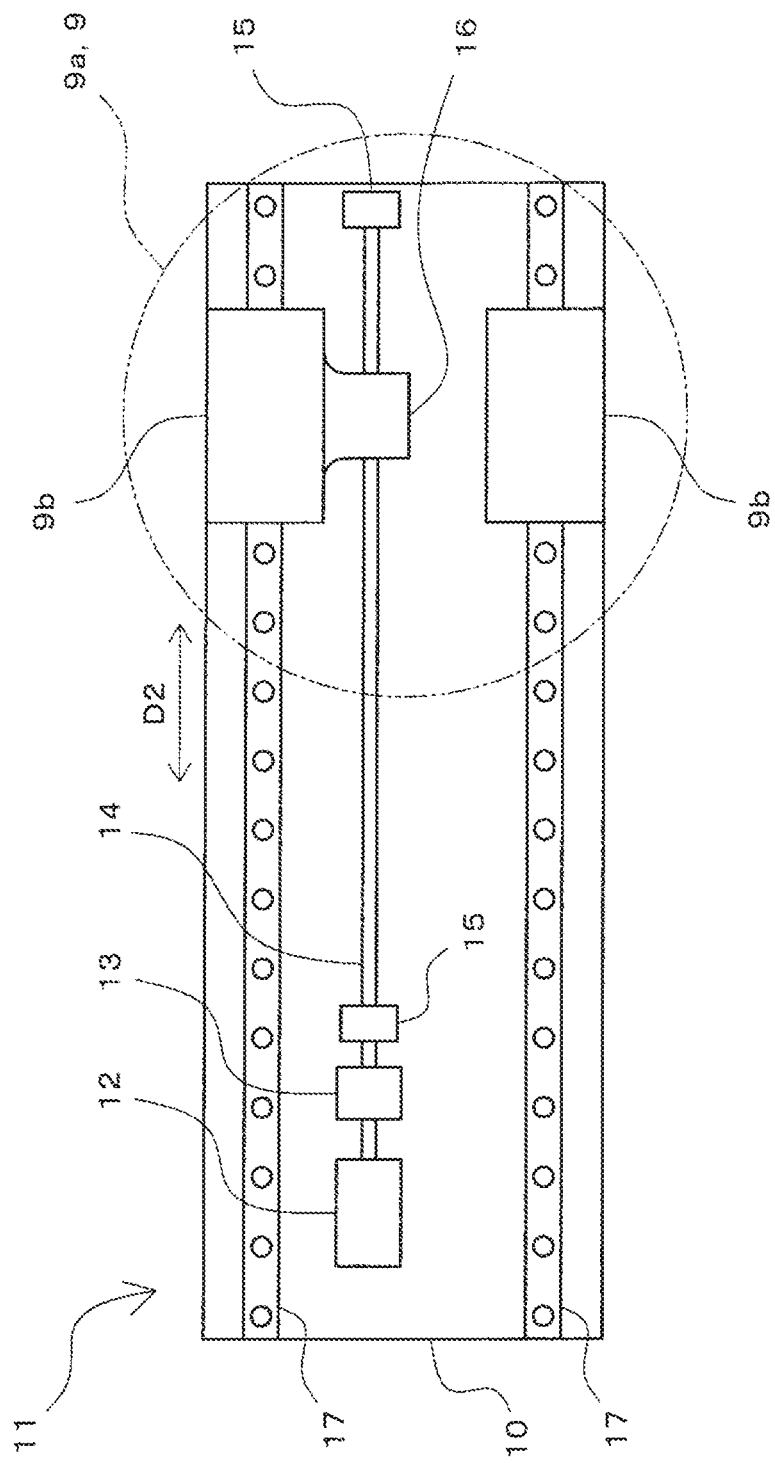
FIG. 2 is a schematic view of a base-side movable part, a first slide section, and a first linear movement mechanism as seen from the bottom side (floor side)

Base-side movable part 9 is rotatable about first axis $Ax_1$ with respect to base 3. Referring to FIG. 1 and FIG. 2, base-side movable part 9 has base plate portion 9a which is formed in a disc shape as seen in the vertical direction, and a pair of guided portions 9b fixed to the upper surface of base plate portion 9a. Base-side movable part 9 is driven to rotate in D1 direction with respect to base 3 by first motor 9c included in robot arm 2.

[Configuration of Linear Movement Assembly]

Figure 3A:
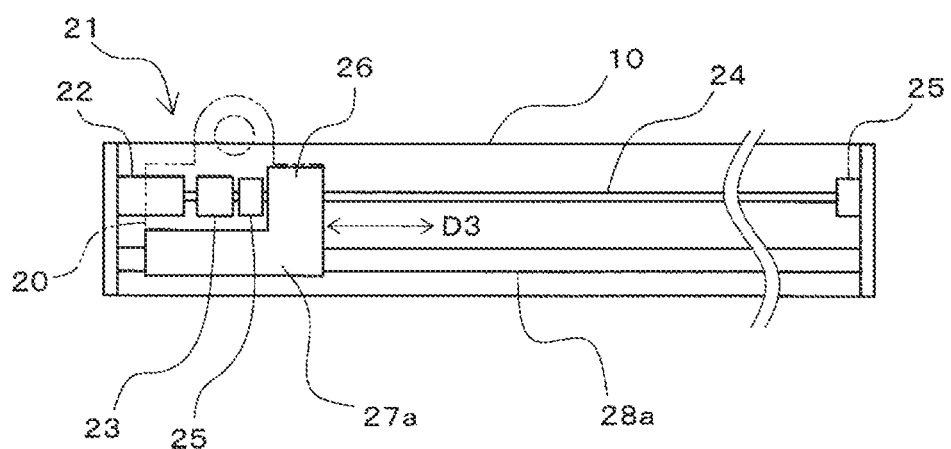
FIG. 3A is a schematic view of one side (the side where a third motor, and a gear reducer are provided) of the first slide section in a widthwise direction as seen from the inside of the first slide section.
Figure 3B:
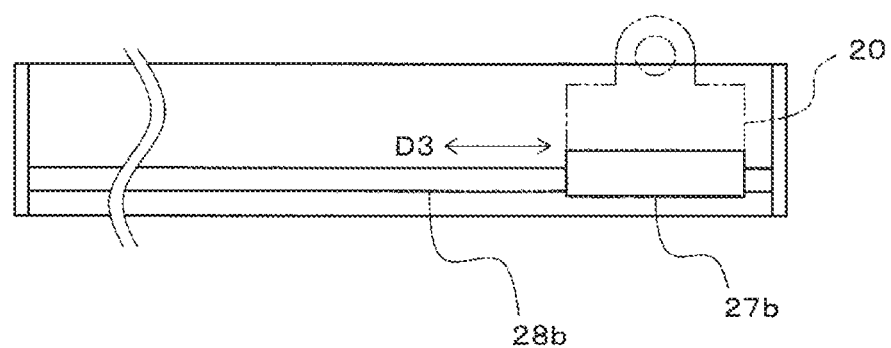
FIG. 3B is a schematic view of the other side (the side where a third motor, a gear reducer are not provided) of the first slide section in a widthwise direction as seen from the inside of the first slide section.

FIG. 2 is a schematic view of first slide section 10 and first linear movement mechanism 11 included in linear movement assembly 5 as seen from the bottom side (floor side). FIG. 3A is a schematic view of one side (the side where third motor 22, gear reducer 23 are provided) of the first slide section 10 in a widthwise direction as seen from the inside of the first slide section 10, and FIG. 3B is a schematic view of the other side (the side where third motor 22, gear reducer 23 are not provided) of the first slide section 10 in a widthwise direction as seen from the inside of the first slide section 10. It is to be noted that in FIG. 2, base-side movable part 9 is illustrated by a dashed-two dotted line. In FIG. 3A and FIG. 3B, second slide section 20 is also illustrated by a dashed-two dotted line.

Linear movement assembly 5 is supported by base 3 via base-side movable part 9 so as to be rotatable about first axis $Ax_1$ (in D1 direction) that extends in the vertical direction. Referring to FIG. 2 and FIGS. 3A and 3B, linear movement assembly 5 includes first slide section 10, first linear movement mechanism 11, second slide section 20, and second linear movement mechanism 21. First slide section 10 is formed in an approximately rectangular box shape having an opening at an upper portion. It is to be noted that base-side movable part 9, first slide section 10, and first linear movement mechanism 11 constitute first slide joint of robot arm 2, and the first slide section, second slide section 20, and second linear movement mechanism 21 constitute second slide joint of robot arm 2.

First slide section 10 is provided to extend horizontally, and the lower portion is supported by base-side movable part 9. First slide section 10 is slidably movable with respect to base-side movable part 9 in the longitudinal direction (in D2 direction) of slide section 10. First slide section 10 is slidably movable between a state where base plate portion 9a is positioned at one end side (the right end side in FIG. 1) of slide section 10, and a state where base plate portion 9a is positioned near the central portion of slide section 10 in the longitudinal direction.

Referring to FIG. 2, first linear movement mechanism 11 has second motor 12, gear reducer 13, screw shaft 14, a pair of bearings 15, nut portion 16, and a pair of rails 17. In first linear movement mechanism 11, a rotational force of the output shaft of second motor 12 is reduced by gear reducer 13, then is transmitted to screw shaft 14. Thus, guided portions 9b formed integrally with nut portion 16 is slidably moved by ball screw mechanism including screw shaft 14 and nut portion 16 in the longitudinal direction of rail 17. Since guided portions 9b are fixed to plate portion 9a, first slide section 10 is slidably moved along with second motor 12, gear reducer 13, and bearings 15 with respect to plate portion 9a in the longitudinal direction of rail 17.

Referring to FIG. 3A, second linear movement mechanism 21 has third motor 22, gear reducer 23, screw shaft 24, a pair of bearings 25, nut portion 26, guided portion 27a, and rail 28a inwardly of one of sidewalls of first slide section 10. Referring to FIG. 3B, second linear movement mechanism 21 has guided portion 27b and rail 28b inwardly of the other sidewall of first slide section 10. In second linear movement mechanism 21, a rotational force of the output shaft of third motor 22 is reduced by gear reducer 23, then is transmitted to screw shaft 24. Thus, guided portion 27a to which nut portion 26 is fixed is slidably moved along rail 28a by ball screw mechanism including screw shaft 24 and nut portion 26. Therefore, second slide section 20 supported by guided portion 27a is slidably moved in the longitudinal direction of first slide section 10 (in D3 direction). Also, second slide section 20 is supported by guided portion 27b which is slidably movable along rail 28b provided in parallel to rail 28a. Consequently, second slide section 20 is supported by a pair of rails 28a, 28b via a pair of guided portions 27a, 27b, and is slidably moved along the pair of rails 28a, 28b.

[Configuration of Wrist Assembly]

Referring to FIG. 1, wrist assembly 6 includes linear movement assembly-side movable part 30, fifth motor 31, roll movable part 32, sixth motor 33, pitch movable part 34, and seventh motor 35.

(Linear movement assembly-side movable part 30 is the movable part that is provided nearest to linear movement assembly 5 in wrist assembly 6. Linear movement assembly-side movable part 30 is coupled to second slide section 20 via first joint 36, and is rotatable about second axis $Ax_2$ (in D4 direction) as a horizontal axis, which extends in a direction that is parallel to a horizontal plane and perpendicular to the longitudinal direction of first slide section 10. In other words, wrist assembly 6 is coupled to linear movement assembly 5 via first joint 36. Linear movement assembly-side movable part 30 is driven to rotate about second axis $Ax_2$ by fourth motor 37 provided corresponding to first joint 36.

Roll movable part 32 is coupled to linear movement assembly-side movable part 30 via second joint 38, and is rotatable about third axis $Ax_3$ (in D5 direction) that extends in a direction perpendicular to second axis $Ax_2$. Roll movable part 32 is driven to rotate about third axis $Ax_3$ by fifth motor 31 provided corresponding to second joint 38. Roll movable part 32 is driven to rotate in this manner, thereby enabling table 8 to move (roll operation) about a roll axis.

Pitch movable part 34 is coupled to roll movable part 32 via third joint 39, and is rotatable about fourth axis $Ax_4$ (in D6 direction) that extends in a direction perpendicular to third axis $Ax_3$. Pitch movable part 34 is driven to rotate about fourth axis $Ax_4$ by sixth motor 33 provided corresponding to third joint 39. Pitch movable part 34 is driven to rotate in this manner, thereby enabling table 8 to move (pitch operation) about a pitch axis.

Seventh motor 35 is provided in between pitch movable part 34 and one end portion of table 8 in the longitudinal direction. Table 8 is driven to rotate about fifth axis $Ax_5$ extending in a direction perpendicular to fourth axis $Ax_4$, by seventh motor 35. This enables table 8 to move (yaw operation) about a yaw axis.

As described above, robot arm 2 includes joints that are rotatable or slidably movable in D1 to D7 directions. However, since slide movement in D direction and D3 direction is along the same line, robot arm 2 has six degrees of freedom (five rotational degrees of freedom and one linear degree of freedom). Also, wrist assembly 6 included in robot arm 2 enables table 8 to rotate in D5 direction (roll direction), D6 direction (pitch direction), and D7 direction (yaw direction). Thus, wrist assembly 6 has three degrees of freedom.

[Configuration of Motors]

Each of motors 9c, 12, 22, 31, 33, 35, 37 included in robotic operation table 1 according to the first implementation is formed of a non-excitation operation electromagnetic brake and a servo motor having a position detector. In each of the motors, after a position detector detects that each movable part driven by the motor has predetermined position and posture, an electromagnetic brake is operated, thereby enabling robot arm 2 to maintain desired position and posture. It is to be noted that each of motors used for the robotic operation table according to this implementation and the second to seventh implementations described below operates movable parts via a gear reducer.

It is to be noted that for instance, a servo motor is used as an electric motor, however, without being limited to this, other electric motors may be used. Also, as a position detector, an encoder which detects a rotational angle and a direction of a motor is used, however, without being limited to this, a resolver, a potentiometer or the like may be used. Also, as an electromagnetic brake, a non-excitation operation electromagnetic brake is preferable, however, without being limited to this, an excitation operation electromagnetic brake may be used.

Using robotic operation table 1 configured as described above allows patient P placed on table 8 to be moved between desired positions. Specifically, for instance, as an example, patient P can be moved between a test position at which patient P placed on table 8 is examined, and an operation position at which an operation is performed for patient P by a doctor. Moving patient P in an operating room using robotic operation table 1 in this manner allows the table to be moved more smoothly without giving a strong vibration to the patient, as compared with the case where a patient is moved by a table with a caster, for instance. In addition, it is possible to avoid formation of an entangled portion between chords associated with medical equipment and tubes associated with medical implements present in a great number on the floor of in a medical room, and to avoid jolting of the table when the table is moved over the entangled portion, and thus the safety and movement efficiency can be improved.

[Operation of Robotic Operation Table]

Figure 4A:
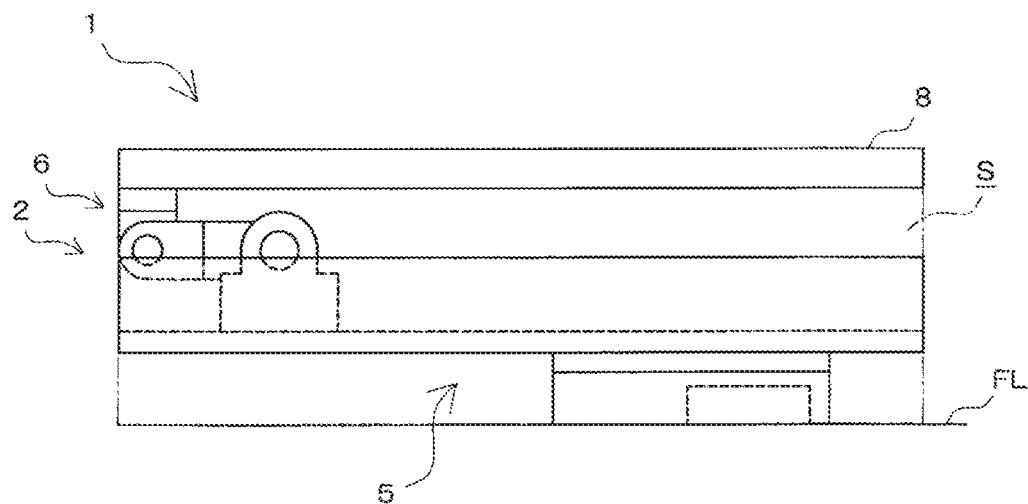
FIG. 4A is a view of a state of a robot arm in a first posture as seen from the lateral side, and the view illustrates a state of the table positioned at a lowest position.
Figure 4B:
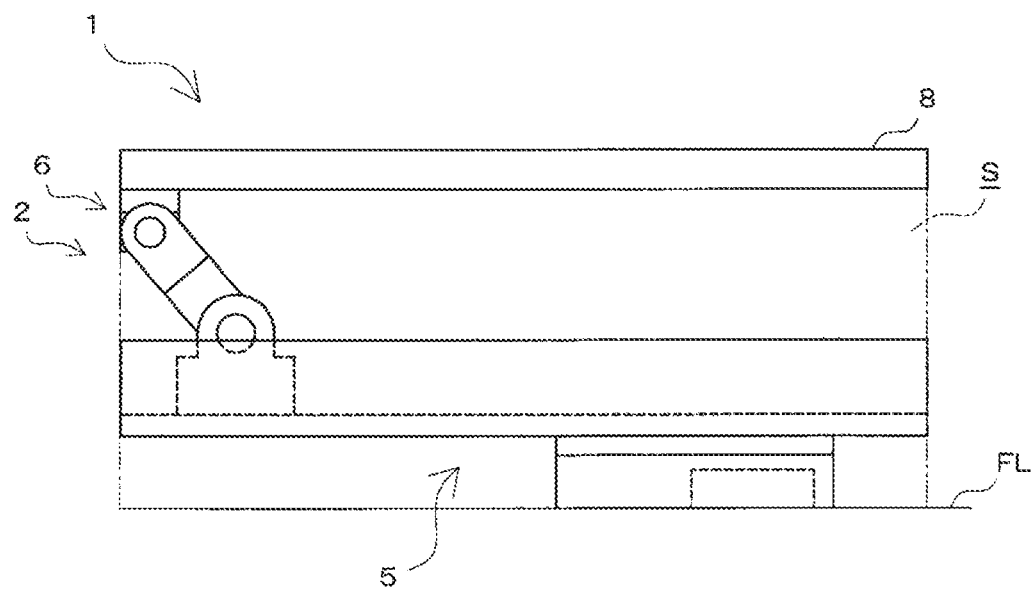
FIG. 4B is a view of a state of a robot arm in a first posture as seen from the lateral side, and the view illustrates a state of the table positioned slightly above the lowest position.

FIG. 4A and FIG. 4B are both views of a state of robot arm 2 in the first posture as seen from the lateral side, FIG. 4A is a view illustrating a state of table 8 positioned at a lowest position (descent position), and FIG. 4B is a view illustrating a state of table 8 lifted upward from the lowest position (state of being positioned at an ascent position). It is to be noted that the lowest position refers to the lowest position among possible height positions of table 8 with reference to floor FL.

Referring to FIG. 4A and FIG. 4B, in a state where robot arm 2 takes the first posture, robot arm 2 is stored in storage space S that is a space under table 8. In other words, in a state where robot arm 2 takes the first posture, robot arm 2 is hidden under table 8 and is invisible as seen from above. In this state, table 8 is positioned at the first position. That is, the first position refers to any position in which robot arm 2 is hidden under table 8 and is invisible as seen from above. It is to be noted that the first position includes any position between the lowest position (descent position) and an ascent position at which table 8 is lifted from the lowest position. In robotic operation table 1, driving the movable parts (such as second slide section 20, and linear movement assembly-side movable part 30) as needed allows table 8 to be moved vertically between the lowest position and the ascent position, while table 8 is being positioned at the first position. The movable parts (such as first slide section 10, second slide section 20, and linear movement assembly-side movable part 30) of robot arm 2 are rotated or slidably moved, and robot arm 2 takes the second posture in which at least part of robot arm 2 horizontally protrudes from storage space S, thereby moving table 8 from the first position to the second position. In a state where table 8 is positioned at the second position, robot arm 2 protrudes from table 8 and is exposed as seen from above. That is, the second position refers to a position in which at least part of robot arm 2 protrudes from table 8 and is exposed as seen from above.

The operation of moving table 8, between multiple positions, supported by robot arm 2 according to this implementation is described with reference to FIG. 5 to FIG. 7.

Figure 5:
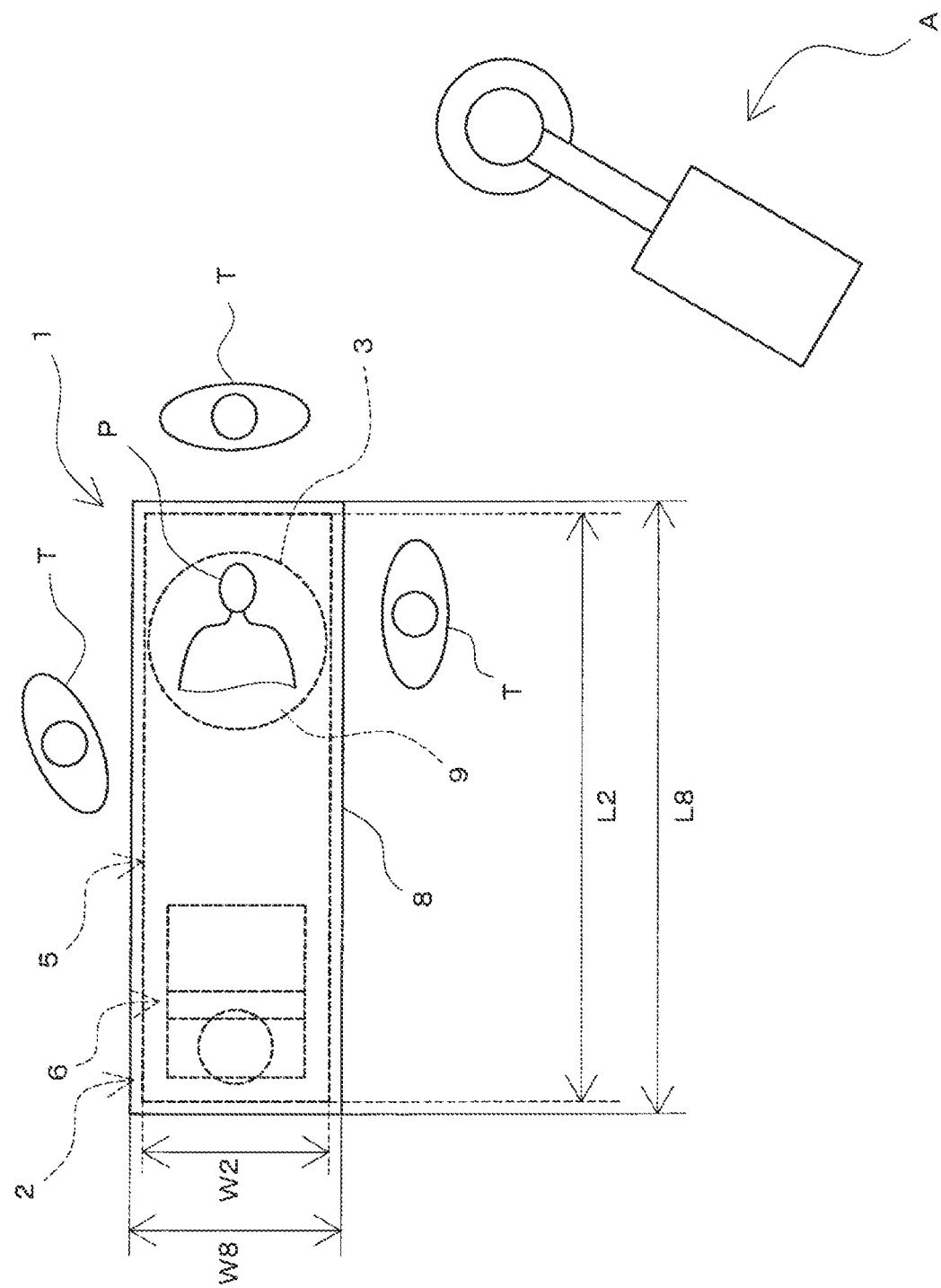
FIG. 5 is a schematic view of an operating room, in which a robotic operation table is set, as seen from above, and the view illustrates the manner in which a table, on which a patient is placed, is positioned at an operation position.
Figure 6:
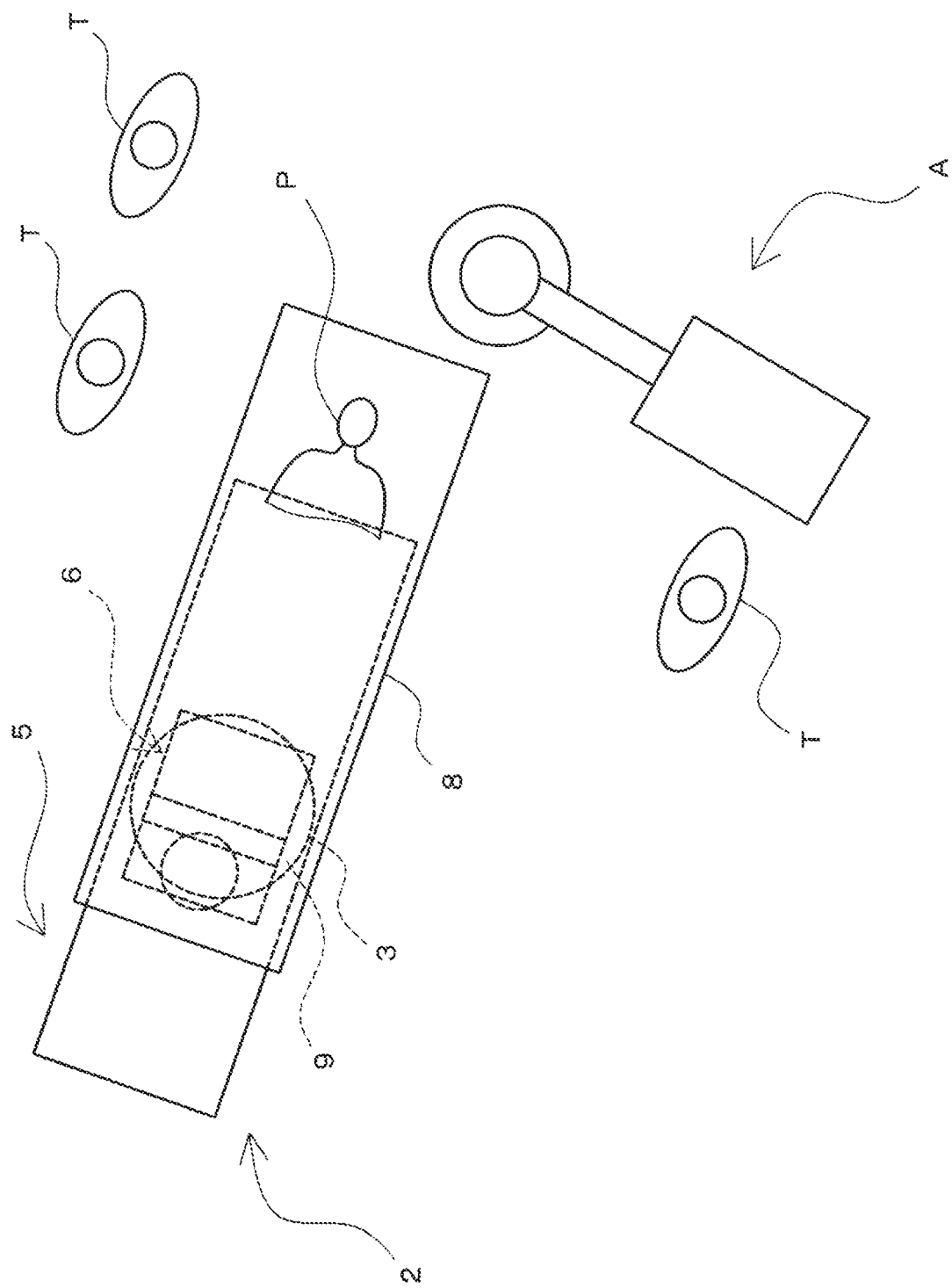
FIG. 6 is a schematic view of an operating room, in which a robotic operation table is set, as seen from above, and the view illustrates the manner in which the table is being moved from an operation position to a test position.

FIG. 5 to FIG. 7 are each a schematic view of an operating room, in which robotic operation table 1 is set, as seen from above. FIG. 5 is a view illustrating the manner in which table 8, on which patient P is placed, is positioned at the first position, FIG. 6 is a view illustrating the manner in which table 8 is being moved from the first position to the second position (test position), and FIG. 7 is a view illustrating a state of a patient transported to the test position. It is to be noted that the position of table 8 in FIG. 5 may be an operation position, and table 8 is returned to the original first position (operation position) from the test position of FIG. 7 to the position of FIG. 5 by operation of each movable part in a reverse direction, and immediately after a test, a doctor can check test results and treat the patient at the operation position. It is to be noted that as testing device A, FIG. 5 to FIG. 7 schematically illustrate X-ray equipment used for angio test.

Movement of table 8 between the positions by robot arm 2 can be achieved by, for instance, giving an instruction to control device 7 to move table 8 in a predetermined direction using an operation device and causing each movable part of robot arm 2 to move. Specifically, robot arm 2 moves table 8 only during the time when a user gives a movement instruction to control device 7 using an operation device. Also, when positions such as an operation position and a test position are pre-stored in control device 7, for instance, giving a movement instruction to control device by a user using an operation device causes the movable part to operate to move table 8 to a target position, and thus table 8 can be smoothly moved to the target position. Furthermore, when a target position and some positions on a path along which table 8 is desired to be moved are specified in advance, for instance, giving a movement instruction to control device 7 by a user using an operation device enables table 8 to be automatically moved along the desired path to reach the target position. In order to record each position, each position may be directly stored by moving robot arm 2 to an actual target position by an operation device, or may be specified by inputting x, y, z coordinates.

Robotic operation table 1 according to the first implementation can take the first posture and the second posture described above. In robotic operation table 1, changing the posture of robot arm 2 from the first posture to the second posture allows table 8 to be moved from an operation position to a test position.

Referring to FIG. 5, in a state where robotic operation table 1 is positioned at an operation position (in other words, in a state where the first posture is taken), dimension W2 of robot arm 2 in a direction parallel to the widthwise direction of table 8 is less than or equal to width dimension W8 of table 8 (W2≤W8), and dimension L2 of robot arm 2 in a direction parallel to the lengthwise direction of table 8 is less than or equal to length dimension L8 of table 8 (L2≤L8).

Referring to FIG. 5, in robotic operation table 1, in a state where table 8 is positioned at an operation position in an operating room in which robotic operation table 1 is set (in other words, in a state where the first posture is taken), robot arm 2 is stored in storage space S that is a space under table 8. Thus, when an operation is performed for patient P after test, robot arm 2 is stored under table 8, and thus when medical workers T around table 8 carry out work near table 8, robot arm 2 causes no interference with medical workers T. Specifically, in a state where a patient has to be treated by medical workers T, interference between medical workers T and robot arm 2 can be avoided. Also, since table 8 can be moved to a test position away from an operation position by robot arm 2, robotic operation table 1 can be set at a position away from testing device A, and thus it is possible to prevent testing device A from interfering with medical workers T during an operation.

When patient P placed on table 8 is moved to a test position, each movable part of robot arm 2 is driven properly, and patient P is transported to the test position. Specifically, referring to FIG. 5 to FIG. 7, in robot arm 2 in a state where the first posture is taken, base-side movable part 9 is rotated with respect to base 3 so that the head of patient P faces test device A, and first slide section 10 and second slide section 20 are slidably moved toward testing device A so that patient P is transported to the testing device A. Consequently, patient P can be transported to testing device A through the state illustrated in FIG. 6 (see FIG. 7).

It is to be noted that when patient P is transported to testing device A, as described above, first slide section 10 and second slide section 20 are slidably moved toward testing device A. Specifically, first slide section 10 is slidably moved with respect to base-side movable part 9 in the longitudinal direction of first slide section 10, and second slide section 20 is slidably moved with respect to first slide section 10 in the longitudinal direction of first slide section 10. That is, in robotic operation table 1 according to the first implementation, when patient P is transported to testing device A, robot arm 2 positioned under the table 8 does not significantly protrude in a direction perpendicular to the movement direction of table 8 (in the widthwise direction of table 8 in the example illustrated in FIG. 5 to FIG. 7). Consequently, when a patient is transported to testing device A, interference between medical workers T positioned around table 8 and robot arm 2 can be avoided.

When the position of patient P transported to the test position is desired to be finely adjusted with respect to testing device A, it is sufficient that the movable parts (such as linear movement assembly-side movable part 30, roll movable part 32, and pitch movable part 34) included in wrist assembly 6 be driven as needed. Thus, the height of table 8, and the inclination of table 8 toward the roll direction, the pitch direction, and the yaw direction can be adjusted. It is to be noted that in this process, patient P can be positioned more accurately with respect to testing device A by operating linear movement assembly 5, too.

In a hybrid operation performed using robotic operation table 1, after testing of patient P, table 8 is moved to the operation position again, and thus an operation can be performed for patient P based on test results in the same operating room. Specifically, in robot arm 2 in a state where table 8 is transported to the test position, table 8 can be returned to the operation position by properly driving each movable part of robot arm 2. In a state where table 8 is positioned at the operation position like this, robot arm 2 is stored in storage space S under table 8. In other words, robot arm 2 does not horizontally protrude outwardly from storage space S under table 8, and when a doctor performs an operation for patient P, robot arm 2 causes no interference with the doctor. Thus, the operation position allows a doctor to perform an operation with a natural posture for patient P.

Depending on operations, a doctor may perform an operation for a patient in a standing position (standing position posture), or for an operation that takes a long time, a doctor may perform the operation for a patient in a sitting position (sitting position posture). In robotic operation table 1 according to this implementation, driving each movable part properly at the operation position allows the height position of table 8 to be adjusted between the ascent position and the lowest position according to the height of a doctor and the posture of a doctor during an operation. Consequently, according to this implementation, a robotic operation table with high usability can be provided.

In robotic operation table 1 according to this implementation, at an operation position (any position between the lowest position and the ascent position described above), robot arm 2 is stored in storage space S under table 8 regardless of the height position of table 8. Specifically, with robotic-operation table 1, robot arm 2 can be stored in storage space S under table 8 regardless of the height position of table 8 which has been vertically moved to an appropriate height position according to the posture (standing position posture, sitting position posture) of a doctor during an operation.

It is to be noted that in a state with the lowest position, the height position of table 8 according to the first implementation is preferably within a range of 450 to 600 mm, and more preferably within a range of 500 to 600 mm. This height allows an operator to easily perform treatment such as an operation for a patient in a sitting position. Also, in a state with the highest position, the height position of table 8 is preferably within a range of 1000 to 1500 mm. The height of 1000 mm illustrated here is such a height that is needed when a patient is tested by a typical testing device. Also, the movable range of table 8 in the horizontal direction (the movable range of table 8 in the longitudinal direction) is preferably of 1000 to 2500 mm. Table 8 is movable to in any in-plane direction in a horizontal plane around the center of the vertical axis about which base-side movable part 9 is rotated.

[Effect]

As described above, with robotic operation table 1 according to the first implementation, patient P placed on table 8 can be moved to a desired position by operating robot arm 2 as needed. In this manner, it is not necessary to manually move an operation table provided with a caster as in related art, thus problems such as entanglement between cables of the peripheral equipment caused by movement of the operation table, and a failure in applying the brake of the operation table are eliminated. That is, with this configuration, patient P placed on table 8 can be moved to a desired position safely.

Furthermore, in robotic operation table 1, when table 8 is positioned at an operation position, robot arm 2 is stored in storage space S that is a space under table 8. In other words, in this state, robot arm 2 does not horizontally protrude outwardly from storage space S.

Therefore, with robotic operation table 1, it is possible to provide a robotic operation table that can sufficiently ensure the space around table 8 for placing a patient.

In addition, with robotic operation table 1, patient P can be moved linearly in a horizontal direction by linear movement assembly 5. With robotic operation table 1, when table 8 on which patient P is placed is moved to a position away from base 3, robot arm 2 positioned under table 8 does not significantly protrude in a direction perpendicular to the movement direction of table 8. Thus, with this configuration, interference between robot arm 2 operated when table 8 is moved and medical workers T around table 8 can be avoided.

Also, with robotic operation table 1, the position and the posture of patient P placed on table 8 can be adjusted not only by linear movement assembly 5 but also by wrist assembly 6 having three degrees of freedom. Consequently, the position and posture of patient P for whom treatment is performed by medical workers T, and the position and posture of patient P with respect to testing device A can be properly adjusted.

Also, in robotic operation table 1, linear movement assembly 5 supports wrist assembly 6 rotatably about a horizontal axis (second shaft $Ax_2$ with reference to FIG. 1). With this configuration, the height position of table 8 can be properly adjusted by rotating wrist assembly 6 about a horizontal axis.

Also, with robotic operation table 1, the position and posture of table 8 can be adjusted by robot arm 2 which has six degrees of freedom.

Also, with robotic operation table 1, when table 8 is positioned at an operation position, robot arm 2 is stored in storage space S under table 8, and thus robot arm 2 causes no interference. Consequently, a doctor as a medical worker T can perform an operation for patient P with a natural posture near table 8.

Also, with robotic operation table 1, in a state where robot arm 2 takes the first posture, the dimension of robot arm 2 in a direction parallel to the widthwise direction of the table is less than or equal to the width dimension of the table, and the dimension of robot arm 2 in a direction parallel to the lengthwise direction of the table is less than or equal to length dimension of the table. Therefore, robot arm 2 can be securely stored in storage space S that is a space under table 8.

Also, with robotic operation table 1, table 8 can be moved between the descent position and the ascent position, while table 8 is being positioned at the first position. Consequently, the height position of table 8 can be adjusted to a position which allows medical workers T to easily perform treatment for patient P without any interference between robot arm 2 and medical workers T.

Also, with robotic operation table 1, the movable parts (such as first slide section 10, and second slide section 20) are moved so that the posture of robot arm 2 changes from the first posture to the second posture, thereby enabling table 8 to be properly moved to a test position away from base 3.

Also, by equipping with two slide sections (first slide section 10 and second slide section 20) as in robotic operation table 1, it is possible to provide a robotic operation table that can move table 8 to a distant position while avoiding upsizing of robot arm 2.

Also, with robotic operation table 1, since table 8 can be moved about the roll axis, the pitch axis, and the yaw axis by wrist assembly 6 (a roll operation, a pitch operation, and a yaw operation can be performed), patient P can be moved to achieve a desired posture by moving table 8 flexibly.

Also, with robotic operation table 1, since robot arm 2 is configured to cause table 8 to perform a roll operation, a pitch operation, and a yaw operation, the posture of patient P can be flexibly adjusted.

(Modification of First Implementation)

(1) Although first linear movement mechanism 11 and second linear movement mechanism 21 of robotic operation table 1 according to the first implementation are configured using what is called a ball screw structure, without being limited to this, any configuration may be adopted as long as the configuration allows first slide section 10 and second slide section 20 to be slidably movable. For instance, a rack and pinion structure may be adopted as the linear movement mechanism described above, as an example.

(2) Although a description has been given by taking an example of robotic operation table 1 having six degrees of freedom as robotic operation table 1 according to the first implementation, without being limited to this, the degrees of freedom of robotic operation table 1 may be 5 or may be 7 or greater.

(3) In this implementation, a description has been given by taking an example of table 8 having one end in the longitudinal direction supported by robot arm 2. In this manner, table 8 can be moved to a more distant position, and thus the movable range of table 8 can be extended. However, without being limited to this, a configuration may be adopted in which a central portion of table 8 in the longitudinal direction is supported by robot arm 2. Consequently, the strength of supporting table 8 by the robot arm can be increased.

(Second Implementation)

Figure 8A:
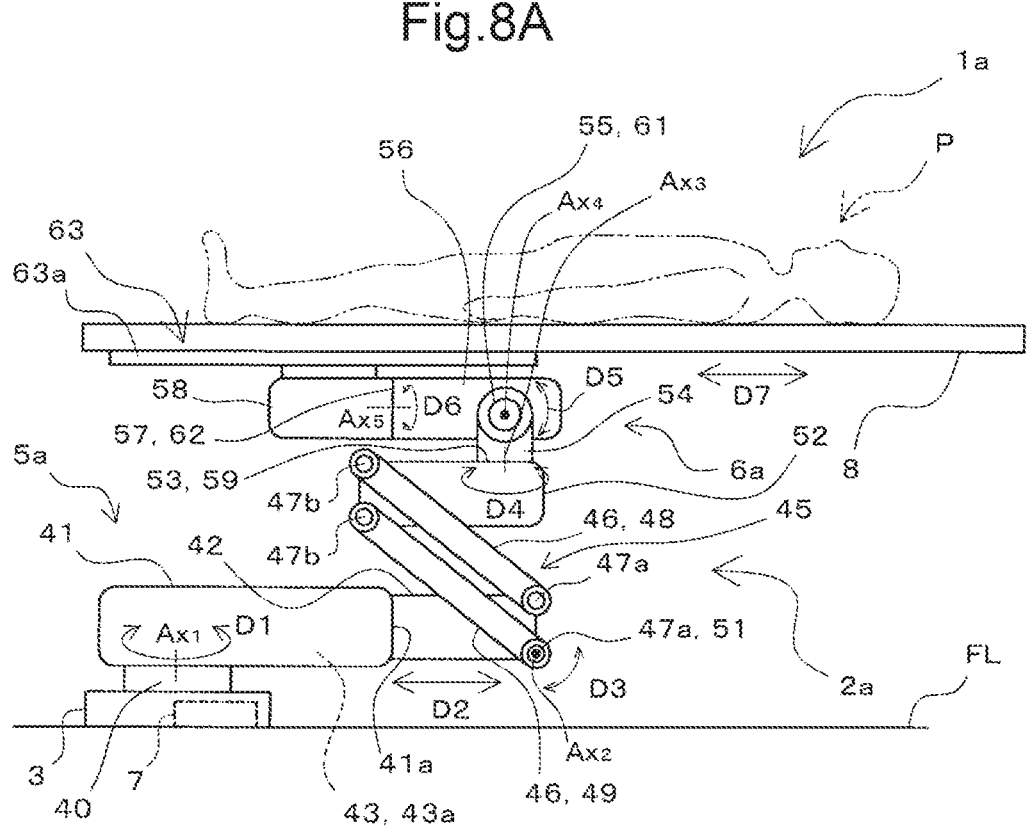
FIG. 8A is a side view of a robotic operation table according to a second implementation, and the view illustrates a state of the table positioned slightly above the lowest position.
Figure 8B:
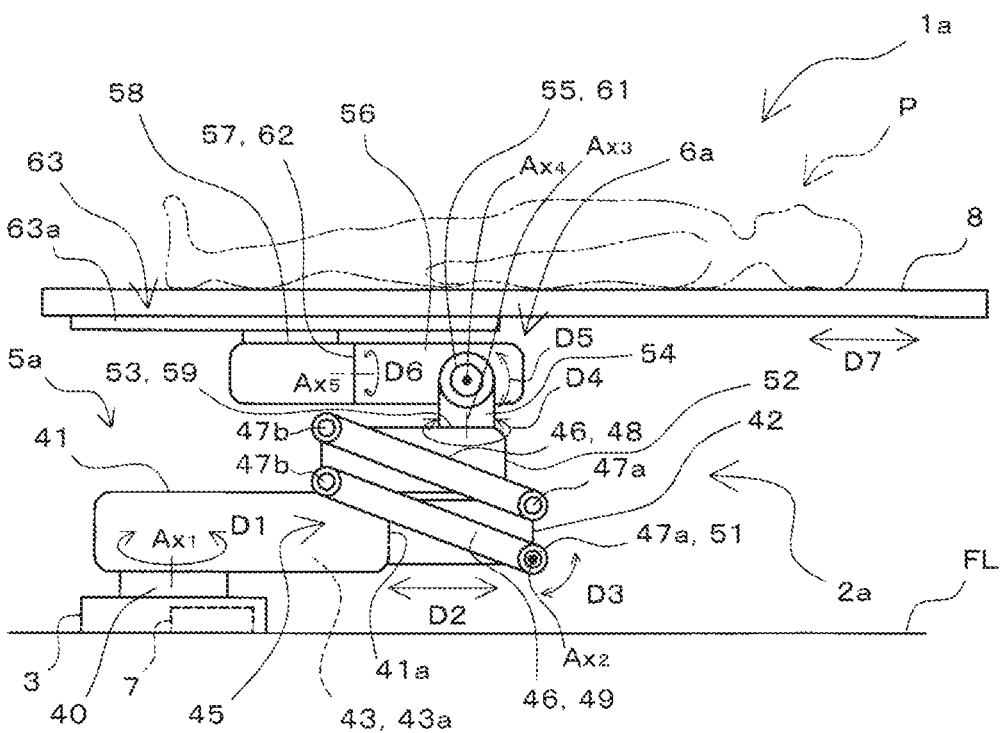
FIG. 8B is a side view of the robotic operation table according to the second implementation, and the view illustrates a state of the table positioned at the lowest position.
Figure 9:
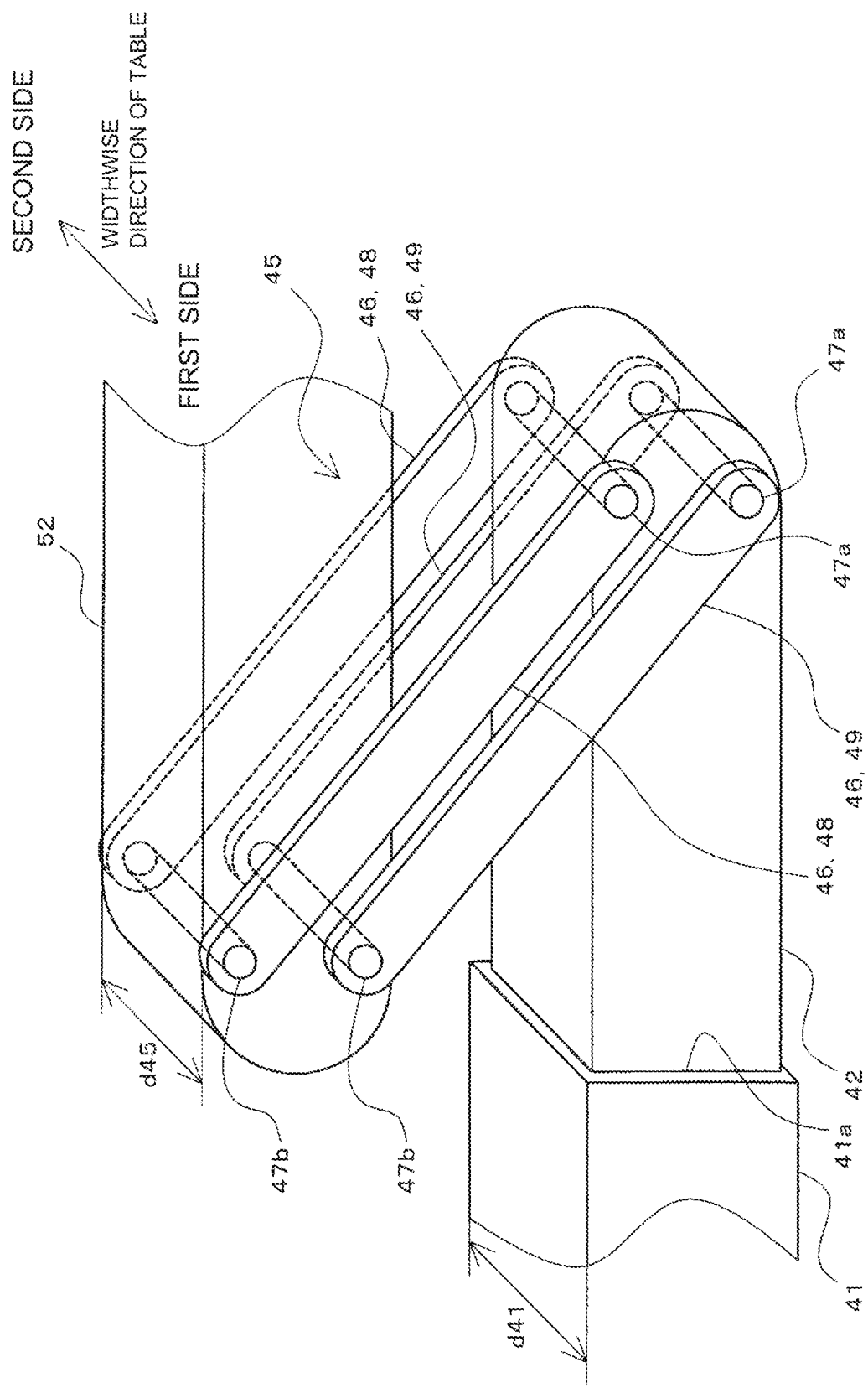
FIG. 9 is a perspective view illustrating an enlarged portion of the robotic operation table illustrated in FIGS. 8A and 8B.

FIGS. 8A and 8B are each a side view of robotic operation table 1a according to a second implementation of the invention, FIG. 8A is a view illustrating a state of table 8 positioned slightly above the lowest position, and FIG. 8B is a view illustrating a state of table 8 positioned at the lowest position. FIG. 9 is a perspective view illustrating an enlarged portion (specifically, the later-described parallel link mechanism 45 and an area in the vicinity in detail) of robotic operation table 1a illustrated in FIGS. 8A and 8B. Robotic operation table 1a includes robot arm 2a, base 3, and table 8. In robotic operation table 1a, one end of robot arm 2a having multiple degrees (seven degrees of freedom in the case of the second implementation) of freedom is supported rotatably about a vertical axis by base 3, whereas the other end of robot arm 2a supports table 8 for placing a patient. The configuration of base 3 is the same as the configuration of base 3 in the first implementation, thus a description is omitted.

Robot arm 2a includes base-side movable part 41, linear movement assembly 5a, parallel link mechanism 45, and wrist assembly 6a.

Base-side movable part 41 is a section formed to extend horizontally, and a lower portion of one end side thereof in the longitudinal direction is linked to base 3 so as to be rotatable about first axis $Ax_1$ (in D1 direction) with respect to base 3. Base-side movable part 41 has opening 41a which is open outwardly, at the other end portion in the longitudinal direction.

[Configuration of Linear Movement Assembly]

Similarly to the case of the first implementation, linear movement assembly 5a is supported by base 3 via base-side movable part 41 so as to be rotatable about first axis $Ax_1$ that extends in the vertical direction. Linear movement assembly 5a is driven to rotate about first axis $Ax_1$ by first motor 40 which is included in robot arm 2 and provided between base 3 and base-side movable part 41. Referring to FIGS. 8A and 8B, linear movement assembly 5 includes linear movement mechanism 43 having slide section 42 and second motor 43a.

Slide section 42 is a section formed in a horizontally elongated rod-like shape, and one end portion thereof is stored in base-side movable part 41 with the longitudinal direction of slide section 42 being parallel to the longitudinal direction of base-side movable part 41. The other end portion of slide section 42 is extendable outwardly from opening 41a of base-side movable part 41, and is retractable into base-side movable part 41. In short, slide section 42 is provided to be slidably movable in the longitudinal direction of base-side movable part 41. Slide section 42 is slid by linear movement mechanism 43 provided between slide section 42 and base-side movable part 41. Linear movement mechanism 43 may be any mechanism as long as the mechanism is capable of slidably moving slide section 42 with respect to base-side movable part 41. As linear movement mechanism 43, for instance, a ball screw mechanism or a rack and pinion mechanism may be used as an example.

[Configuration of Parallel Link Mechanism]

Parallel link mechanism 45 is a link mechanism that links linear movement assembly 5a and wrist assembly 6a. Referring to FIG. 9, parallel link mechanism 45 has four link members 46, two first link shafts 47a, and two second link shafts 47a.

Link members 46 are each formed in a linear shape. The lengths of the link members 46 are the same. In each link member 46, one end portion (lower-side portion) is rotatably coupled to slide section 42 via first link shaft 47a, whereas the other end portion (upper-side portion) is rotatably coupled to linear movement assembly-side movable part 52 via second link shaft 47b. Two out of the four link members are provided at one side of table 8 in the widthwise direction, and the remaining two are provided at the other side of table 8 in the widthwise direction. Four link members 46 include two upper-side link members 48 provided on the upper side, and two lower-side link members 49 provided on the lower side.

First link shaft 47a is a shaft-shaped portion that rotatably links the lower end portion of each link member 46 to the leading end portion of slide section 42. In a state where each link member 46 is linked to slide section 42, each first link shaft 47a extends in the widthwise direction of table 8.

Second link shaft 47b is a shaft-shaped portion that rotatably links the upper end portion of each link member 46 to linear movement assembly-side movable part 52 of wrist assembly 6a. In a state where each link member 46 is linked to linear movement assembly-side movable part 52, each second link shaft 47b extends in the widthwise direction of table 8.

Referring to FIG. 9, in parallel link mechanism 45, distance d45 between the two link members 46 provided at one side (first side) of table 8 in the widthwise direction, and the two link members 46 provided at the other side (second side) of table 8 in the widthwise direction is greater than width dimension d41 (the dimension of table 8 in a direction parallel to the widthwise direction) of base-side movable part 41. This makes it possible to avoid interference between link members 46 and base-side movable part 41, and thus table 8 can be lowered to a low position (see FIG. 8B).

Parallel link mechanisms 45 are driven by third motor 51. Specifically, third motor 51 is provided at each position corresponding to, for instance, first link shafts 47a that link lower-side link members 49 to slide section 42, and third motor 51 drives lower-side link members 49 to rotate about a central axis $Ax_2$ (in D3 direction) of first link shaft 47a.

Thus, each lower-side link member 49 swings around first link shaft 47a as the center, thus wrist assembly 6a linked to the upper end portion of lower-side link member 49 moves vertically. It is to be noted that as lower-side link members 49 are driven to rotate by third motor 51, upper-side link members 48 are also operated in conjunction with lower-side link members 49. Consequently, wrist assembly 6a can be supported securely by the four link members 46 from the lower side.

[Configuration of Wrist Assembly]

Wrist assembly 6a includes linear movement assembly-side movable part 52, fourth motor 53, yaw movable part 54, fifth motor 55, pitch movable part 56, sixth motor 57, roll movable part 58, and table slide mechanism 63.

Linear movement assembly-side movable part 52 is a movable part that is provided nearest to linear movement assembly 5 in wrist assembly 6a. Linear movement assembly-side movable part 52 is provided to extend in a direction parallel to in the longitudinal direction of table 8, and is supported by parallel link mechanism 45 so as to maintain a posture parallel to a horizontal plane. Linear movement assembly-side movable part 52 is moved vertically while being swung by parallel link mechanism 45 that rotates in D3 direction.

Yaw movable part 54 is linked to linear movement assembly-side movable part 5 via first joint 59, and is rotatable about third axis $Ax_3$ (in D4 direction) that extends in the vertical direction. Yaw movable part 54 is driven to rotate about third axis $Ax_3$ by fourth motor 53 provided corresponding to first joint 59. In this manner, yaw movable part 54 is driven to rotate, and thus table 8 can be moved about the yaw axis.

Pitch movable part 56 is linked to yaw movable part 54 via second joint 61, and is rotatable about fourth axis $Ax_4$ (in D5 direction) that extends in a direction perpendicular to third axis $Ax_3$. Pitch movable part 56 is driven to rotate about fourth axis $Ax_4$ by fifth motor 55 provided corresponding to second joint 61. In this manner, pitch movable part 56 is driven to rotate, and thus table 8 can be moved about the pitch axis.

Roll movable part 58 is linked to pitch movable part 56 via third joint 62, and is rotatable about fifth axis $Ax_5$ (in D6 direction) that extends in the longitudinal direction of table 8. Roll movable part 58 is driven to rotate about fifth axis $Ax_5$ by sixth motor 57 provided corresponding to third joint 62. In this manner, roll movable part 58 is driven to rotate, and thus table 8 can be moved about the roll axis.

[Configuration of Table Slide Mechanism]

Table slide mechanism 63 is a mechanism for slidably moving table 8 with respect to roll movable part 58 in the longitudinal direction of table 8 (in D7 direction). In short, table slide mechanism 63 can move table 8 by a one linear degree of freedom. Table slide mechanism 63 is formed using motor 63a or the like. As table slide mechanism 63, for instance, a ball screw mechanism or a rack and pinion mechanism may be adopted. Table 8 is supported to be slidably movable by table slide mechanism 63.

The configuration of each motor in the second implementation is the same as the configuration in the first implementation, thus a description is omitted. Similarly to the case of the first implementation, also in this implementation, each motor operates each movable part via a gear reducer.

As described above, robot arm 2a includes joints that are rotatable or slidably movable in D1 to D7 directions, and thus has seven degrees of freedom (5 rotational degrees of freedom and 2 linear degrees of freedom). Referring to FIGS. 8A and 8B, wrist assembly 6a enables table 8 to be rotated in D4 direction (yaw direction), D5 direction (pitch direction), D6 direction (roll direction) and to be slidably moved in D7 direction. Thus, wrist assembly 6a has four degrees of freedom.

When thus configured robotic operation table 1a is used, similarly to the case of the first implementation described above, the table can be accurately moved to a predetermined target position, and thus the efficiency of the testing and treatment in medical practice can be significantly improved and the safety and movement efficiency can be enhanced.

[Operation of Robotic Operation Table]

The table can be moved between multiple positions within a movable range by robot arm 2a via a freely chosen route according to this implementation. Thus, the table can be moved to a testing device and others along the same path as in FIG. 5 to FIG. 7 which have been described in the first implementation. Specifically, robot arm 2a, which is stored in storage space S under table 8 and takes the first posture, is changed to take the second posture, thereby enabling table 8 to be moved from an operation position to a test position. Conversely, robot arm 2a in the second posture is changed to take the first posture, thereby enabling table 8 to be moved from a test position to an operation position.

[Effect]

As described above, with robotic operation table 1a according to the second implementation, similarly to the case of the first implementation, when table 8 is positioned at an operation position, robot arm 2a is stored in storage space S that is a space under table 8. Thus, it is possible to provide a robotic operation table that can sufficiently ensure the space around table 8 for placing a patient.

(Modification of Second Implementation)

Referring to FIGS. 8A and 8B, in the second implementation, a description has been given by taking an example in which table 8 is rotated in the yaw direction by rotating the movable part (yaw movable part 54) provided on the side of wrist assembly 6a, facing linear movement assembly-side movable part 52 in the yaw direction (D4 direction). However, the invention is not limited to this. Specifically, for instance, as an example, a motor is provided between the movable part (roll movable part 58) provided on the side of wrist assembly 6a, facing table 8, and table slide mechanism 63, and table 8 may be rotated in the yaw direction by the motor.

(Third Implementation)

Figure 10:
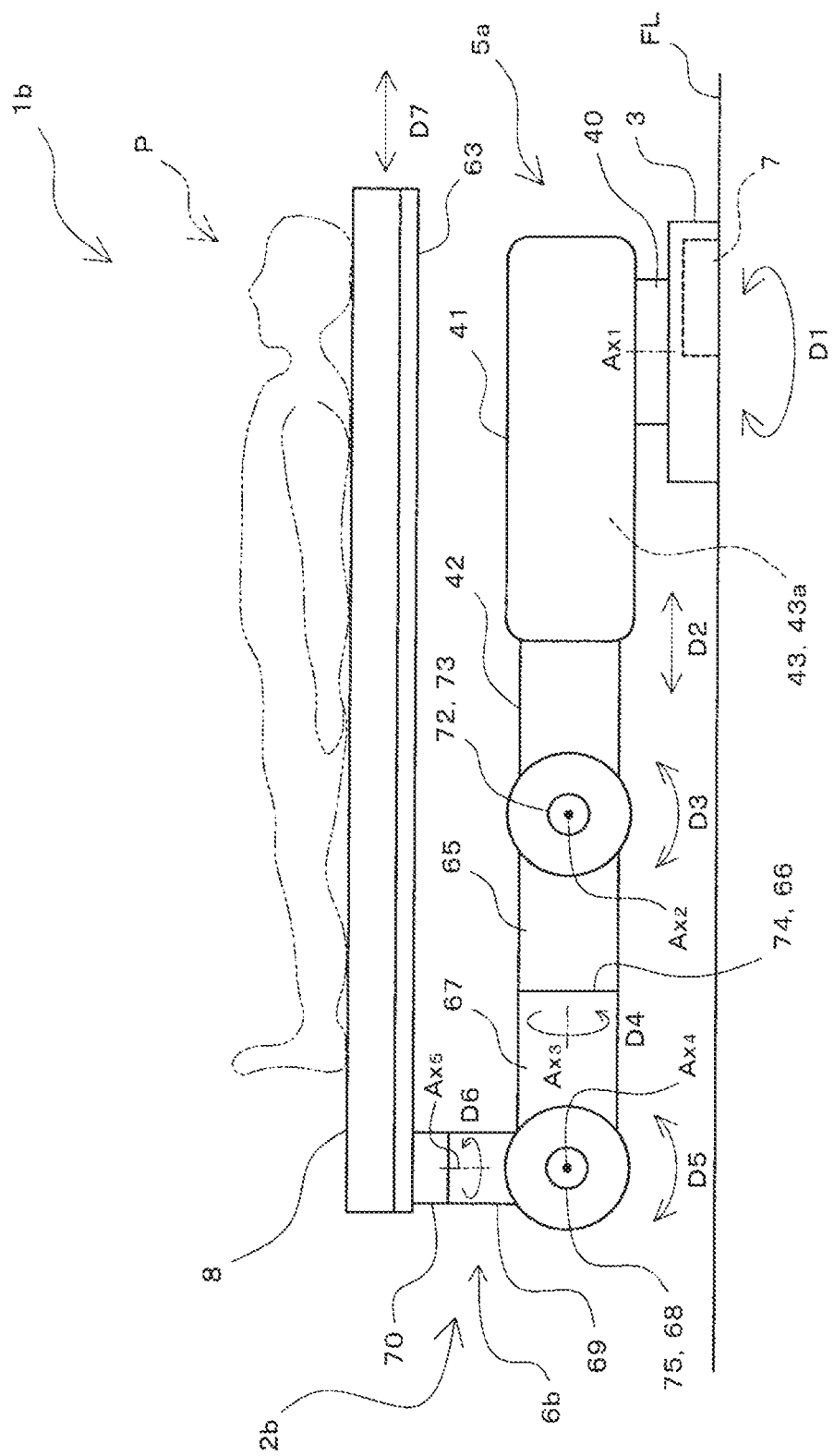
FIG. 10 is a side view of a robotic operation table according to a third implementation.

FIG. 10 is a side view of robotic operation table 1b according to a third implementation of the invention. Robotic operation table 1b includes robot arm 2b, base 3, and table 8. In robotic operation table 1b, one end of robot arm 2b having multiple degrees (seven degrees of freedom in the case of the third implementation) of freedom is supported rotatably about a vertical axis by base 3, whereas the other end of robot arm 2a supports table 8 for placing a patient. The configuration of base 3 is the same as the configuration of base 3 in the first implementation, thus a description is omitted.

Robot arm 2b includes base-side movable part 41, linear movement assembly 5a, and wrist assembly 6b. Among these, the configuration of base-side movable part 41 and linear movement assembly 5a is the same as the configuration of base-side movable part 41 and linear movement assembly 5a in the second implementation, thus a description is omitted.

[Configuration of Wrist Assembly]

Referring to FIG. 10, wrist assembly 6b includes linear movement assembly-side movable part 65, fourth motor 66, roll movable part 67, fifth motor 68, pitch movable part 69, sixth motor 70, and table slide mechanism 63. Among these, the configuration of table slide mechanism 63 is the same as the configuration of table slide mechanism 63 in the second implementation, thus a description is omitted.

Linear movement assembly-side movable part 65 is the movable part that is provided nearest to linear movement assembly 5a in wrist assembly 6b. Linear movement assembly-side movable part 65 is linked to slide section 42 via first joint 72, and is rotatable about second axis $Ax_2$ (in D3 direction) that extends in a direction which is parallel to a horizontal plane and perpendicular to the longitudinal direction of slide section 42. In other words, wrist assembly 6b is coupled to linear movement assembly 5a via first joint 72. Linear movement assembly-side movable part 65 is driven to rotate about second axis $Ax_2$ by third motor 73 provided corresponding to first joint 72.

Roll movable part 67 is coupled to linear movement assembly-side movable part 6 via second joint 74, and is rotatable about third axis $Ax_3$ (in D4 direction) that extends in a direction perpendicular to second axis $Ax_2$. Roll movable part 67 is driven to rotate about third axis $Ax_3$ by fourth motor 66 provided corresponding to second joint 72. In this manner, roll movable part 67 is driven to rotate, and thus table 8 can be moved about the roll axis.

Pitch movable part 69 is coupled to roll movable part 67 via third joint 75, and is rotatable about fourth axis $Ax_4$ (in D5 direction) that extends in a direction perpendicular to third axis $Ax_3$. Pitch movable part 69 is driven to rotate about fourth axis $Ax_4$ by fifth motor 68 provided corresponding to third joint 75. In this manner, pitch movable part 69 is driven to rotate, and thus table 8 can be moved about the pitch axis.

Sixth motor 70 is provided between pitch movable part 69 and one end portion of table slide mechanism 63 in the longitudinal direction. Table 8 is driven to rotate about fifth axis $Ax_5$ extending in a direction perpendicular to fourth axis $Ax_4$, by sixth motor 70. Thus, table 8 can be moved about the yaw axis.

The configuration of each motor in the third implementation is the same as the configuration in the first implementation, thus a description is omitted. Similarly to the case of the first implementation, also in this implementation, each motor operates each movable part via a gear reducer.

As described above, robot arm 2b includes joints that are rotatable or slidably movable in D1 to D7 directions, and thus has seven degrees of freedom (5 rotational degrees of freedom and 2 linear degrees of freedom). Referring to FIG. 10, wrist assembly 6b enables table 8 to be rotated in D4 direction (roll direction), D5 direction (pitch direction), D6 direction (yaw direction) and to be slidably moved in D7 direction. Thus, wrist assembly 6b has four degrees of freedom.

When thus configured robotic operation table 1b is used, similarly to the case of the first and second implementations described above, the table can be accurately moved to a predetermined target position, and thus the efficiency of the testing and treatment in medical practice can be significantly improved and the safety and movement efficiency can be enhanced.

[Operation of Robotic Operation Table]

The table can be moved between multiple positions within a movable range by robot arm 2b via a freely chosen route according to this implementation. Thus, the table can be moved to a testing device and others along the same path as in FIG. 5 to FIG. 7 which have been described in the first implementation. Specifically, robot arm 2b, which is stored in storage space S under table 8 and takes the first posture, is changed to take the second posture, thereby enabling table 8 to be moved from an operation position to a test position. Conversely, robot arm 2b in the second posture is changed to take the first posture, thereby enabling table 8 to be moved from a test position to an operation position.

[Effect]

As described above, with robotic operation table 1b according to the third implementation, similarly to the case of the first and second implementations, when table 8 is positioned at the first position, robot arm 2b is stored in storage space S that is a space under table 8. Thus, it is possible to provide a robotic operation table that can sufficiently ensure the space around table 8 for placing a patient.

(Fourth Implementation)

Figure 11:
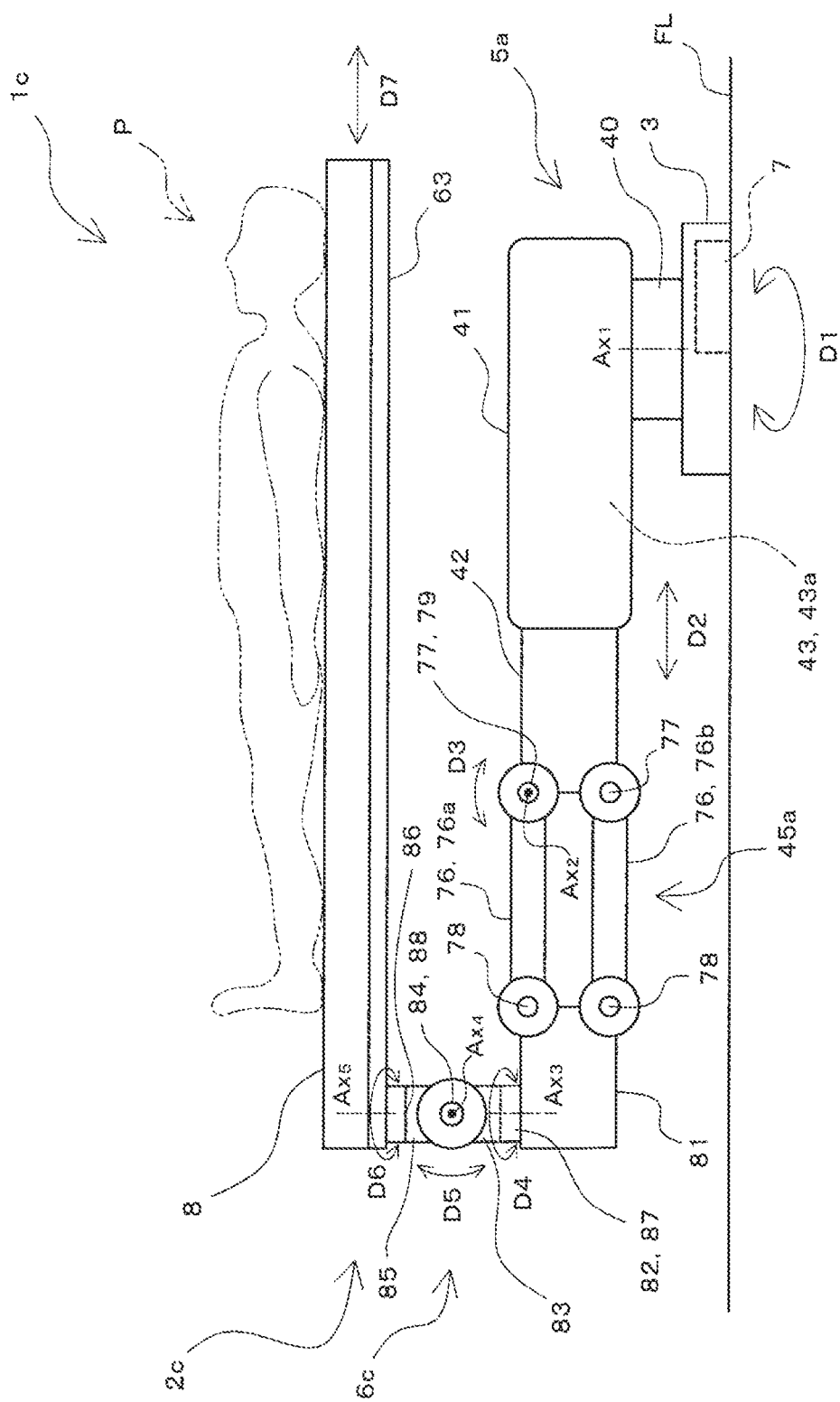
FIG. 11 is a side view of a robotic operation table according to a fourth implementation.
Figure 12:
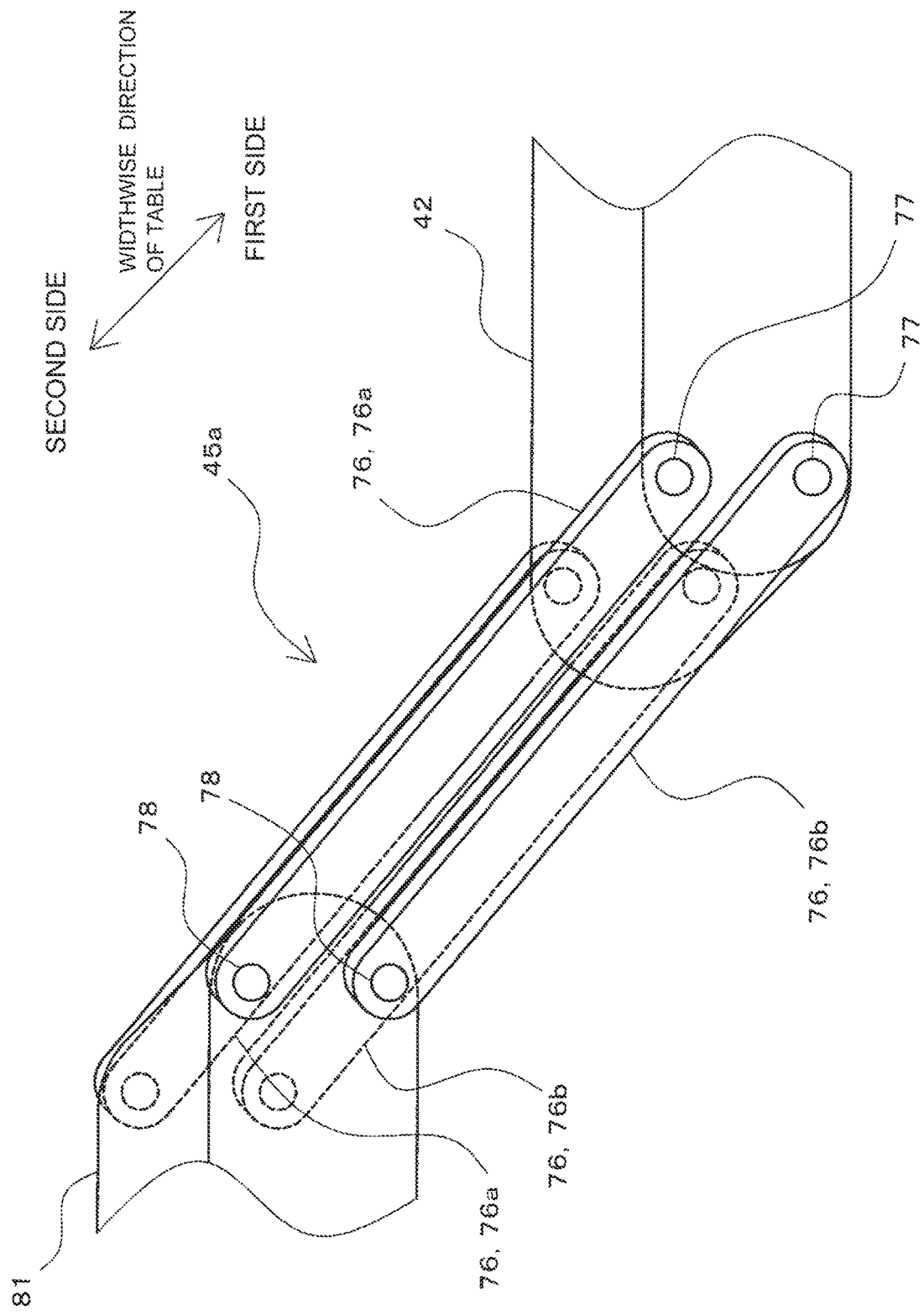
FIG. 12 is a perspective view illustrating an enlarged portion of the robotic operation table illustrated in FIG. 11.

FIG. 11 is a side view of robotic operation table 1c according to a fourth implementation of the invention. FIG. 12 is a perspective view illustrating an enlarged portion (specifically, the later-described parallel link mechanism 45a and an area in the vicinity in detail) of robotic operation table 1c illustrated in FIG. 11. Robotic operation table 1c includes robot arm 2c, base 3, and table 8. In robotic operation table 1c, one end of robot arm 2c having multiple degrees (seven degrees of freedom in the case of the fourth implementation) of freedom is supported rotatably about a vertical axis by base 3, whereas the other end of robot arm 2a supports table 8 for placing a patient. The configuration of base 3 is the same as the configuration of base 3 in the first implementation, thus a description is omitted.

Robot arm 2c includes base-side movable part 41, linear movement assembly 5a, parallel link mechanism 45a, and wrist assembly 6c. Among these, the configuration of base-side movable part 41 and linear movement assembly 5a is the same as the configuration of base-side movable part 41 and linear movement assembly 5a in the second implementation, thus a description is omitted.

[Configuration of Parallel Link Mechanism]

Parallel link mechanism 45a is a link mechanism that links linear movement assembly 5a and wrist assembly 6c. As illustrated in FIG. 12, parallel link mechanism 45a has four link members 76, two first link shafts 77, and two second link shafts 78.

Link members 76 are each formed in a linear shape. The lengths of the link members 76 are the same. In each link member 76, one end portion (portion near slide section 42) is rotatably coupled to slide section 42 via first link shaft 77, whereas the other end portion (portion near linear movement assembly-side movable part 81) is rotatably coupled to linear movement assembly-side movable part 81 via second link shaft 78. Two out of the four link members 76 are provided at one side of table 8 in the widthwise direction, and the remaining two are provided at the other side of table 8 in the widthwise direction. Four link members 76 include two upper-side link members 76a provided on the upper side, and two lower-side link members 76b provided on the lower side.

Parallel link mechanisms 45a are driven by third motor 79. Specifically, third motor 79 is provided at, for instance, a position corresponding to one of two link shafts 77 provided in the vertical direction, and third motor 79 drives one part (the upper side in FIG. 11) of link members 76 to rotate about a central axis $Ax_2$ (in D3 direction) of link shaft 77. Thus, link members 76 on the upper side swing around link shaft 77 as the center, thus wrist assembly 6c moves vertically. It is to be noted that as link members 76 on the upper side are driven to rotate by third motor 79, link members 76 on the lower side are also operated in conjunction with link members 76 on the upper side.

[Configuration of Wrist Assembly]

Wrist assembly 6c includes linear movement assembly-side movable part 81, fourth motor 82, roll movable part 83, fifth motor 84, pitch movable part 85, sixth motor 86, and table slide mechanism 63. The configuration of table slide mechanism 63 is the same as the configuration of table slide mechanism 63 in the second and third implementations, thus a description is omitted.

Linear movement assembly-side movable part 81 is the movable part that is provided nearest to linear movement assembly 5a in wrist assembly 6c. Linear movement assembly-side movable part 81 is supported by parallel link mechanism 45a so as to maintain a posture parallel to a horizontal plane. Rotation of parallel link mechanism 45a in D3 direction causes linear movement assembly-side movable part 81 to move vertically.

Roll movable part 83 is coupled to linear movement assembly-side movable part 81 via first joint 87, and is rotatable about third axis $Ax_3$ (in D4 direction) that extends in the vertical direction. Roller movable part 83 is driven to rotate about third axis $Ax_3$ by fourth motor 82 provided corresponding to first joint 87. In FIG. 11, pitch movable part 85 described later in detail is rotated in D5 direction, and roll movable part 83 is rotated in D4 direction with table 8 inclined in the pitch direction, and thereby table 8 can be rotated in the roll direction.

Pitch movable part 85 is coupled to roll movable part 83 via second joint 88, and is rotatable about fourth axis $Ax_4$ (in D5 direction) that extends in a direction perpendicular to third axis $Ax_3$. Pitch movable part 85 is driven to rotate about fourth axis $Ax_4$ by fifth motor 84 provided corresponding to second joint 88. In this manner, pitch movable part 85 is driven to rotate, and thus table 8 can be moved about the pitch axis.

Sixth motor 86 is provided between pitch movable part 85 and one end portion of table slide mechanism 63 in the longitudinal direction. Table 8 is driven to rotate about fifth axis $Ax_5$ extending in a direction perpendicular to fourth axis $Ax_4$, by sixth motor 86. Thus, table 8 can be moved about the yaw axis.

The configuration of each motor in the fourth implementation is the same as the configuration in the first implementation, thus a description is omitted. Similarly to the case of the first implementation, also in this implementation, each motor operates each movable part via a gear reducer.

As described above, robot arm 2c includes joints that are rotatable or slidably movable in D1 to D7 directions, and thus has seven degrees of freedom (5 rotational degrees of freedom and 2 linear degrees of freedom). Also, wrist assembly 6c enables table 8 to be rotated in the roll direction, the pitch direction, the yaw direction, and to be slidably moved in D7 direction. Thus, wrist assembly 6c has four degrees of freedom.

When thus configured robotic operation table 1c is used, similarly to the case of the first to third implementations described above, the table can be accurately moved to a predetermined target position, and thus the efficiency of the testing and treatment in medical practice can be significantly improved and the safety and movement efficiency can be enhanced.

[Operation of Robotic Operation Table]

The table can be moved between multiple positions within a movable range by robot arm 2c via a freely chosen route according to this implementation. Thus, the table can be moved to a testing device and others along the same path as in FIG. 5 to FIG. 7 which have been described in the first implementation. Specifically, robot arm 2c, which is stored in storage space S under table 8 and takes the first posture, is changed to take the second posture, thereby enabling table 8 to be moved from an operation position to a test position. Conversely, robot arm 2c in the second posture is changed to take the first posture, thereby enabling table 8 to be moved from a test position to an operation position.

[Effect]

As described above, with robotic operation table 1c according to the fourth implementation, similarly to the case of the first to third implementations, when table 8 is positioned at an operation position, robot arm 2c is stored in storage space S that is a space under table 8. Thus, it is possible to provide a robotic operation table that can sufficiently ensure the space around table 8 for placing a patient.

(Fifth Implementation)

Figure 13:
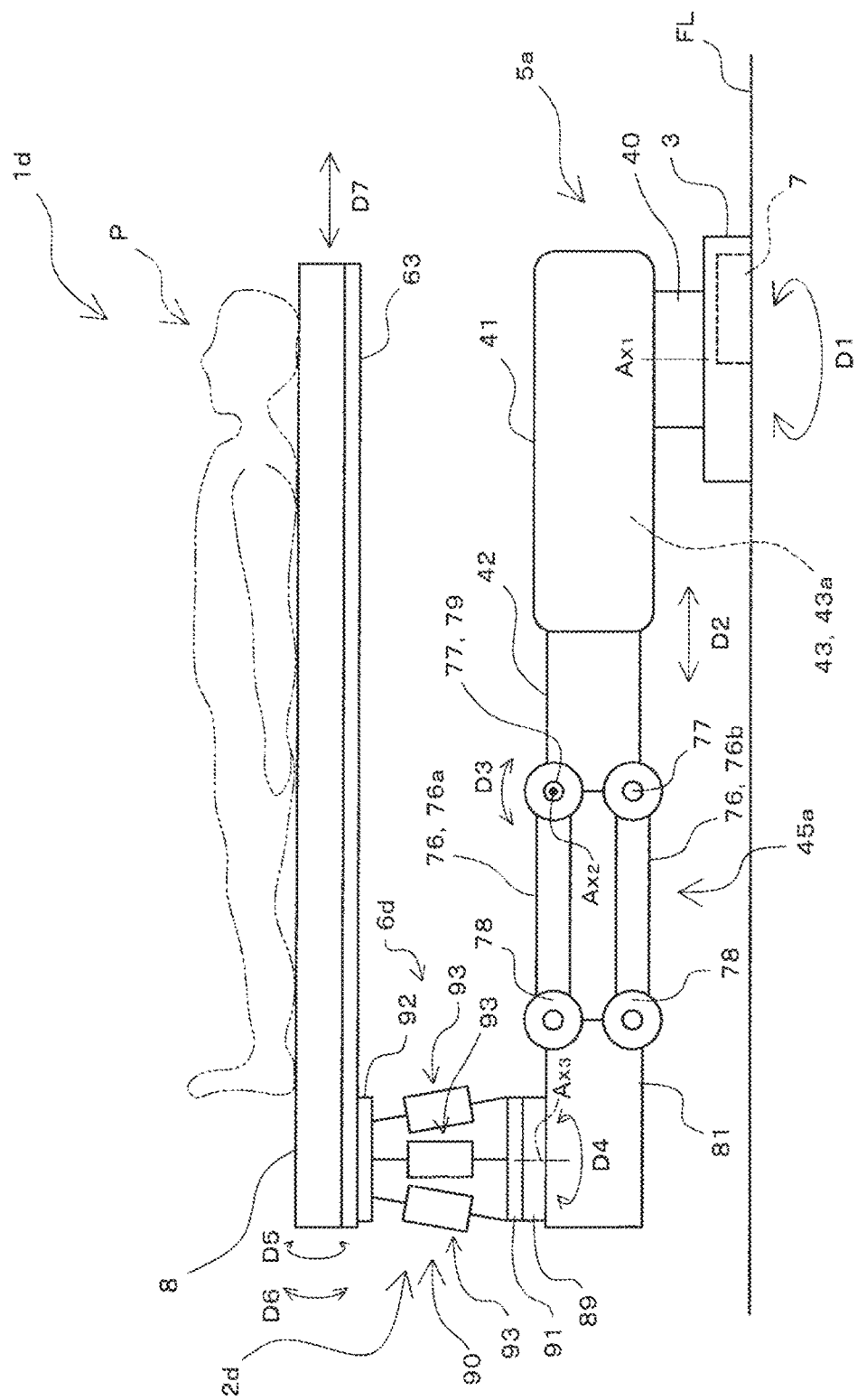
FIG. 13 is a side view of a robotic operation table according to a fifth implementation.

FIG. 13 is a side view of robotic operation table 1d according to a fifth implementation of the invention. Robotic operation table 1d includes robot arm 2d, base 3, and table 8. In robotic operation table 1d, one end of robot arm 2d having multiple degrees of freedom is supported rotatably about a vertical axis by base 3, whereas the other end of robot arm 2a supports table 8 for placing a patient. The configuration of base 3 is the same as the configuration of base 3 in the first implementation, thus a description is omitted.

Robot arm 2d includes base-side movable part 41, linear movement assembly 5a, parallel link mechanism 45a, and wrist assembly 6d. Robotic operation table 1d according to the fifth implementation differs from robotic operation table 1c according to the fourth implementation in that the configuration of the wrist assembly is different. Hereinafter, the configuration of wrist assembly 6d is mainly described, and a description of other configurations is omitted.

[Configuration of Wrist Assembly]

Wrist assembly 6d includes linear movement assembly-side movable part 81, fourth motor 89, parallel link mechanism 90, and table slide mechanism 63. Among these, the configuration of linear movement assembly-side movable part 81 and table slide mechanism 63 is the same as the configuration of those in the fourth implementation, thus a description is omitted.

Fourth motor 89 is provided between an upper portion of linear movement assembly-side movable part 81 and parallel link mechanism 90 described later in detail. Fourth motor 89 drives parallel link mechanism 90 to rotate about third axis $Ax_3$ (in D4 direction) that extends in the vertical axis direction. Thus, table 8 can be moved about the yaw axis.

Figure 14:
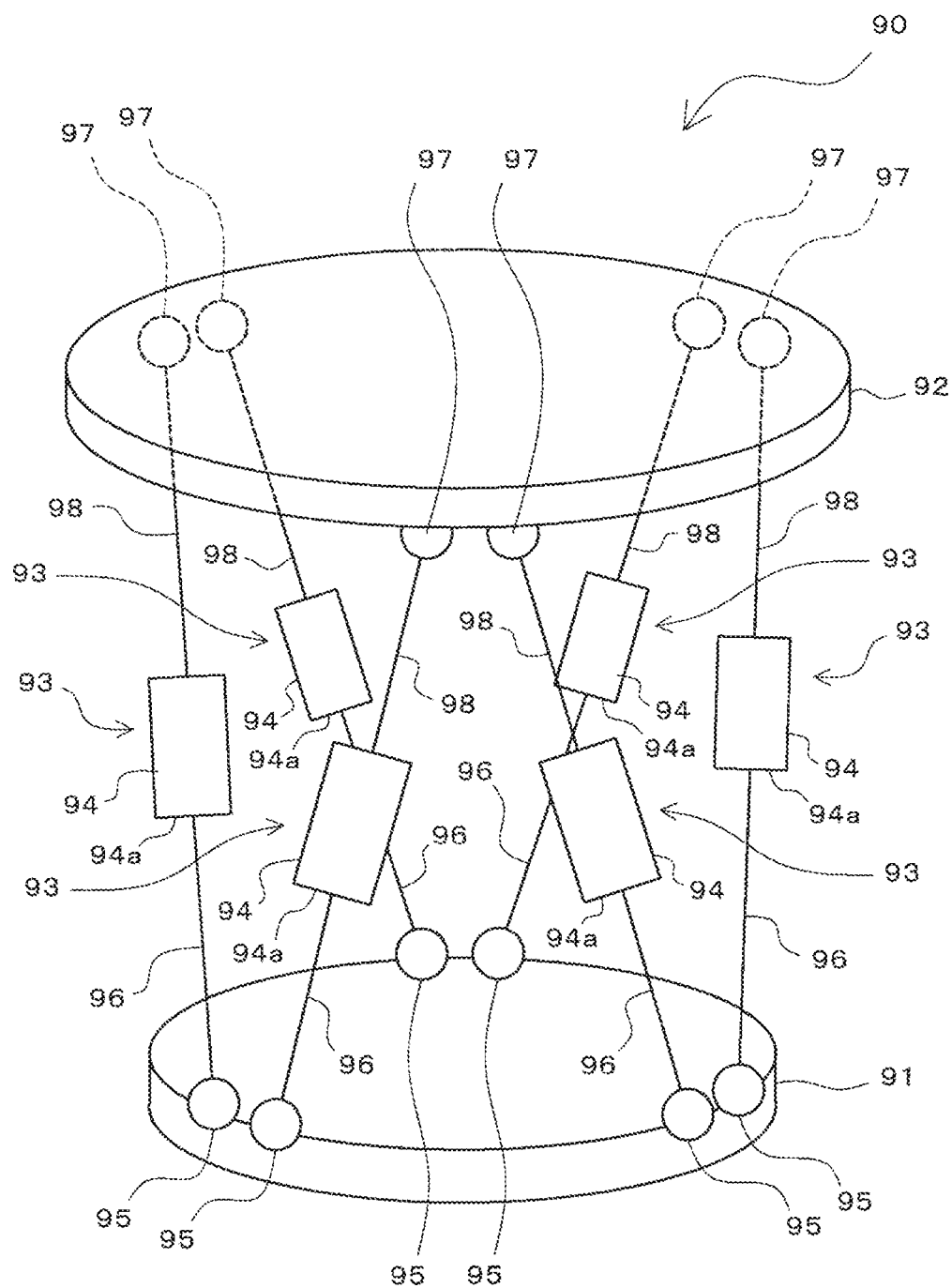
FIG. 14 is a perspective view schematically illustrating the parallel link mechanism illustrated in FIG. 13.

FIG. 14 is a perspective view schematically illustrating parallel link mechanism 90. Parallel link mechanism 90 in this implementation is what is called Stewart-platform-type parallel link mechanism 90. Parallel link mechanism 90 includes base stand 91, movable plate 92, and six cylinders 93. It is to be noted that FIG. 13 illustrates only three cylinders 93 to avoid complicated drawings.

Base stand 91 is formed in a flat plate-like shape. Fourth motor 89 described above is provided between base stand 91 and linear movement assembly-side movable part 81. Base stand 91 is driven to rotate about third axis $Ax_3$ (in D4 direction) by fourth motor 89.

Similarly to base stand 91, movable plate 92 is formed in a flat plate-like shape. Movable plate 92 supports the back side of table 8 via table slide mechanism 63.

Each cylinder 93 includes cylinder portion 94 formed in a cylindrical shape, base stand-side rod 96 that couples bottom 94a of cylinder portion 94 to base stand 91 via adjustable joint 95, and extending and retracting 98 having one end portion stored in cylinder portion 94 and the other end portion fixed to movable plate 92 via adjustable joint 97. It is to be noted that as cylinder 93, any of the following types of cylinder may be used: an electric cylinder, an air cylinder, and a hydraulic pressure cylinder.

In parallel link mechanism 90, a projection amount of extending and retracting 98 from cylinder portion 94 is adjusted according to an instruction from control device 7. Thus, the posture of movable plate 92 (in other words, posture of table 8) with respect to base stand 91 can be adjusted. Parallel link mechanism 90 in this implementation is a Stewart-platform-type parallel link mechanism. Specifically, in parallel link mechanism 90, a projection amount of extending and retracting 98 is adjusted as needed, thereby enabling movable plate 92, that is, table 8 to be moved in at least the roll direction (D5 direction) and the pitch direction (D6 direction). In other words, parallel link mechanism 90 can cause table 8 to perform a roll operation and a pitch operation.

The configuration of each motor in the fifth implementation is the same as the configuration in the first implementation, thus a description is omitted. Similarly to the case of the first implementation, also in this implementation, each motor operates each movable part via a gear reducer.

As described above, robot arm 2d is movable in D1 to D7 directions. Referring to FIG. 13, wrist assembly 6d enables table 8 to be moved at least in D4 direction (roll direction), D5 direction (pitch direction), D6 direction (yaw direction), and to be slidably moved in D7 direction. Thus, wrist assembly 6d has four degrees of freedom.

When thus configured robotic operation table 1d is used, similarly to the case of the first to fourth implementations described above, the table can be accurately moved to a predetermined target position, and thus the efficiency of the testing and treatment in medical practice can be significantly improved and the safety and movement efficiency can be enhanced.

[Operation of Robotic Operation Table]

The table can be moved between multiple positions within a movable range by robot arm 2d via a freely chosen route according to this implementation. Thus, the table can be moved to a testing device and others along the same path as in FIG. 5 to FIG. 7 which have been described in the first implementation. Specifically, robot arm 2d, which is stored in storage space S under table 8 and takes the first posture, is changed to take the second posture, thereby enabling table 8 to be moved from an operation position to a test position. Conversely, robot arm 2d in the second posture is changed to take the first posture, thereby enabling table 8 to be moved from a test position to an operation position.

[Effect]

As described above, with robotic operation table 1d according to the fifth implementation, similarly to the case of the first to fourth implementations, when table 8 is positioned at an operation position, robot arm 2d is stored in storage space S that is a space under table 8. Thus, it is possible to provide a robotic operation table that can sufficiently ensure the space around table 8 for placing a patient.

Also, in robotic operation table 1d, as described above, Stewart-platform-type parallel link mechanism 90 is adopted for wrist assembly 6d. Parallel link mechanism 90 is excellent in stiffness. Therefore, with robotic operation table 1d according to the fifth implementation, it is possible to provide a robotic operation table in which vibration is not easily transmitted to patient P at the time of movement or operation.

(Sixth Implementation)

Figure 15:
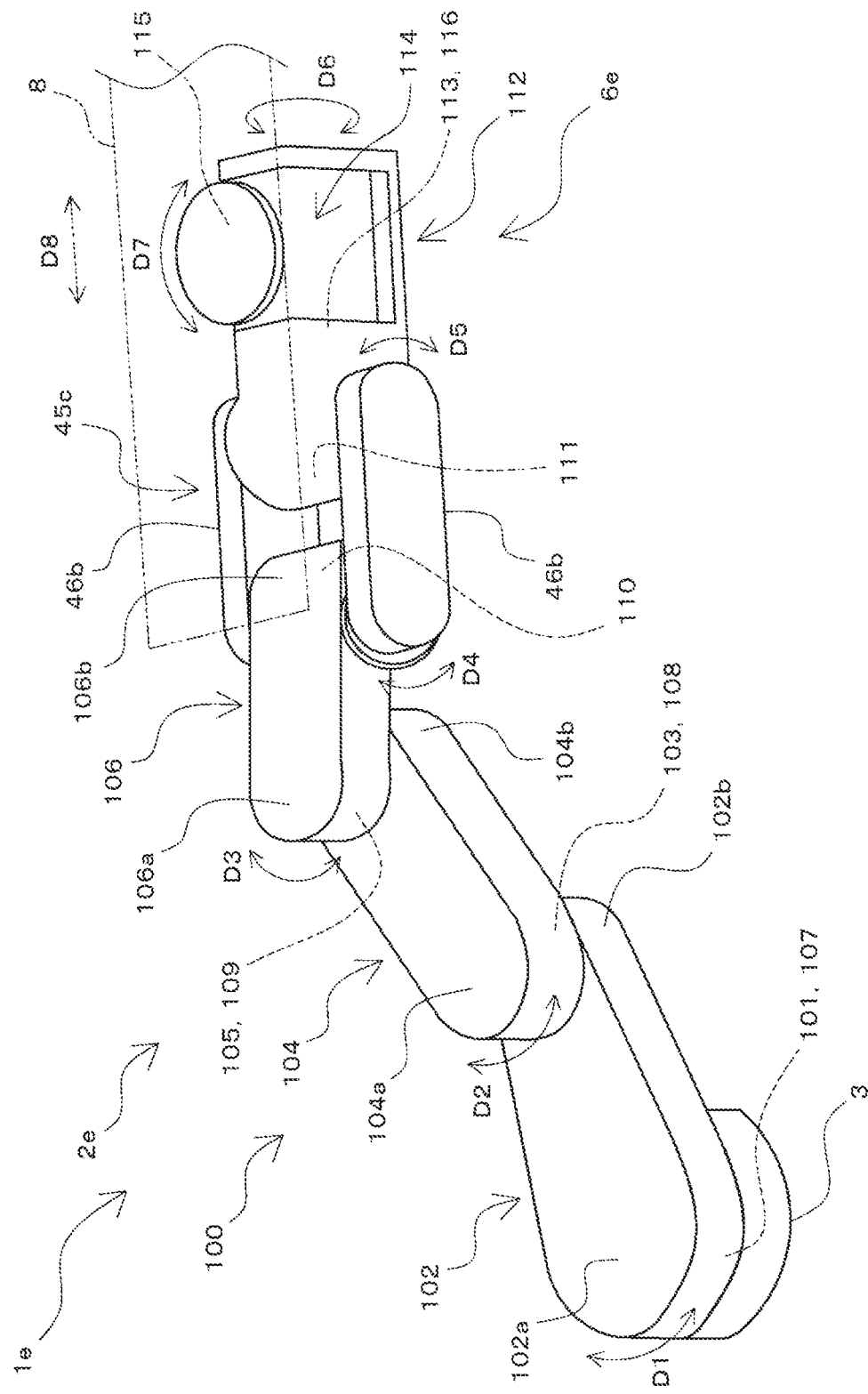
FIG. 15 is a perspective view schematically illustrating a robotic operation table according to a sixth implementation.
Figure 16A:
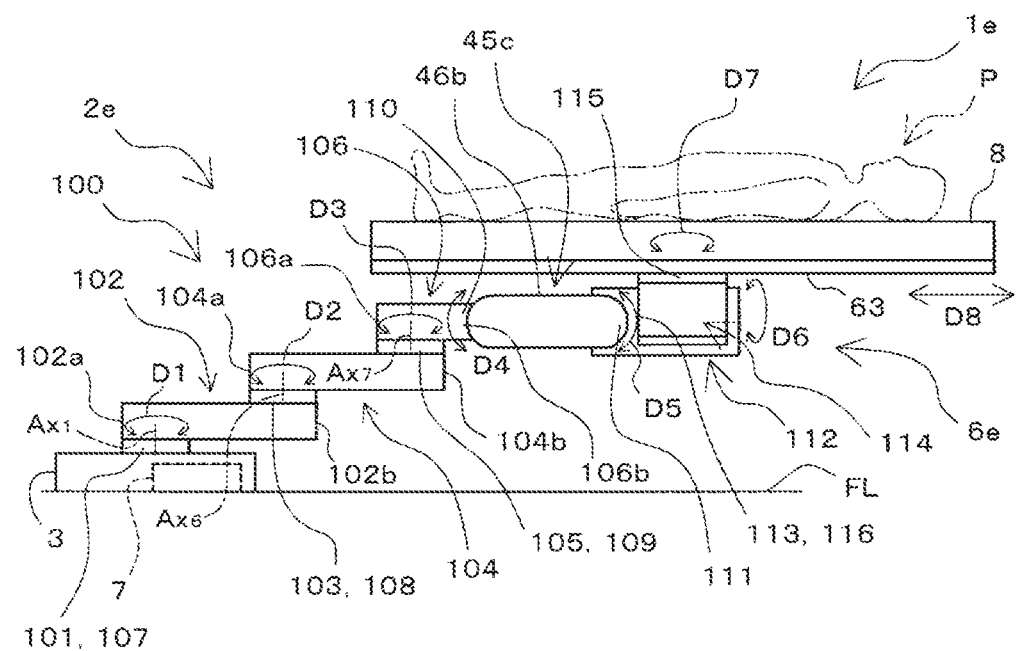
FIG. 16A is a side view of the robotic operation table illustrated in FIG. 15, and the view illustrates the robot arm in a second posture.
Figure 16B:
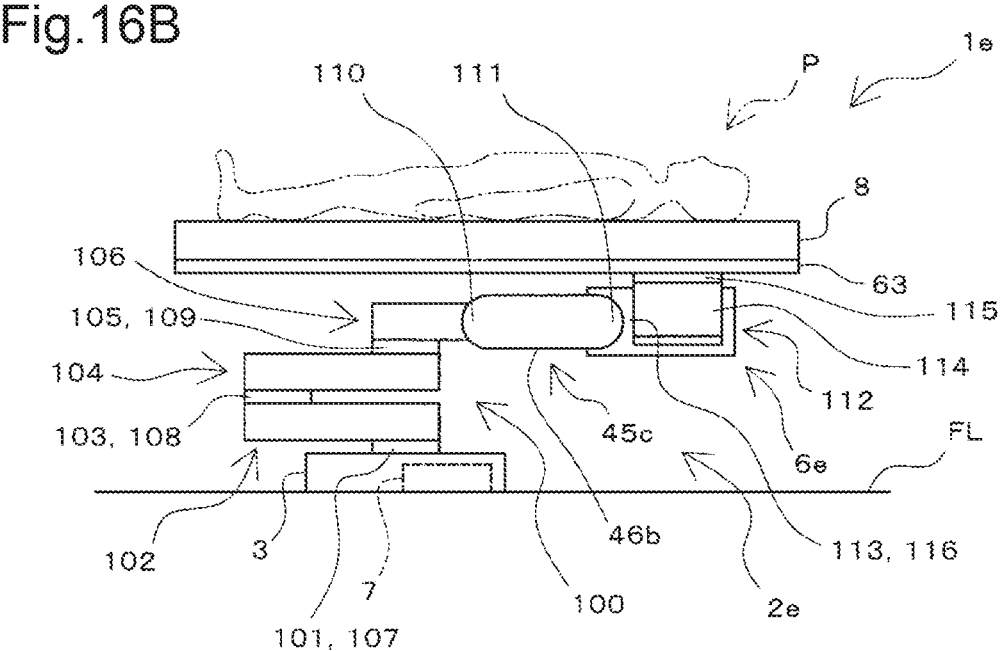
FIG. 16B is a side view of the robotic operation table illustrated in FIG. 15, and the view illustrates the robot arm in the first posture.

FIG. 15 is a perspective view schematically illustrating robotic operation table 1e according to a sixth implementation of the invention. FIGS. 16A and 16B are each a side view of robotic operation table 1e illustrated in FIG. 15, FIG. 16A is a view of robot arm 2e in the second posture, and FIG. 16B is a view of robot arm 2e in the first posture. Robotic operation table 1e includes robot arm 2e, base 3, and table 8. In robotic operation table 1e, one end of robot arm 2e having multiple degrees (eight degrees of freedom in the case of the sixth implementation) of freedom is supported rotatably about a vertical axis by base 3, whereas the other end of robot arm 2e supports table 8 for placing a patient. The configuration of base 3 is the same as the configuration of base 3 in the first implementation, thus a description is omitted. It is to be noted that in FIG. 15, table 8 is illustrated by a dashed-two dotted line.

Robot arm 2e includes horizontal multi-articulated assembly 100, parallel link mechanism 45c, and wrist assembly 6e. Among these, the configuration of base 3 is the same as the configuration of base 3 in the first implementation, thus a description is omitted.

[Configuration of Horizontal Multi-Articulated Assembly]

Horizontal multi-articulated assembly 100 has movable parts 102, 104, 106 adjacent two of which are rotatable about a vertical axis, and each of movable parts 102, 104, 106 is rotated within a horizontal plane, thereby enabling table 8 to be moved within a horizontal plane.

Horizontal multi-articulated assembly 100 includes first motor 101, first movable part 102, second motor 103, second movable part 104, third motor 105, and third movable part 106.

First movable part 102 is formed in an elongated plate-like shape having a predetermined thickness in a vertical direction as seen from above. First movable part 102 is coupled to base 3 via first joint 107 at one end 102a, and is rotatable about a vertical axis $Ax_1$ (in D1 direction). In other words, one end 102a of first movable part 102 is supported by base 3 so as to be rotatable about a vertical axis $Ax_1$. First movable part 102 is driven to rotate in D1 direction by first motor 101 provided corresponding to first joint 107.

Second movable part 104 is formed in an elongated plate-like shape having a predetermined thickness in a vertical direction as seen from above. Second movable part 104 is coupled, at one end 104a, to the other end 102b of first movable part 102 via second joint 108, and is rotatable about second vertical axis $Ax_6$ (in D2 direction). In other words, one end 104a of second movable part 104 is supported by the other end 102b of first movable part 102 so as to be rotatable about second vertical axis $Ax_6$. Second movable part 104 is driven to rotate in D2 direction by second motor 103 provided corresponding to second joint 108.

Third movable part 106 is formed in an elongated plate-like shape having a predetermined thickness in a vertical direction as seen from above. Third movable part 106 is coupled, at one end 106a, to the other end 104b of second movable part 104 via third joint 109, and is rotatable about third vertical axis $Ax_7$ (in D3 direction). In other words, one end 106a of third movable part 106 is supported by the other end 104b of second movable part 104 so as to be rotatable about third vertical axis $Ax_7$. Third movable part 106 is driven to rotate in D3 direction by third motor 105 provided corresponding to third joint 109.

[Configuration of Parallel Link Mechanism]

Parallel link mechanism 45c is a link mechanism that links horizontal multi-articulated assembly 100 and wrist assembly 6e together. Parallel link mechanism 45c has two link members 46b.

Each link member 46b is formed in an elongated plate-like shape having a predetermined thickness. Both ends of each link member 46b are rotatably linked to the other end 106b of third movable part 106 and wrist assembly 6e (specifically, pitch movable part 112 of wrist assembly 6e) respectively, via a link shaft.

Parallel link mechanism 45c is driven by fourth motor 110. Specifically, fourth motor 110 is provided at a position corresponding to the other end 106b of third movable part 106, and drives each link member 46b to rotate about a link axis (in D4 direction). This causes parallel link mechanism 45c to swing in D4 direction, thus wrist assembly 6e can be moved vertically.

[Configuration of Wrist Assembly]

Wrist assembly 6e includes fifth motor 111, pitch movable part 112, sixth motor 113, roll movable part 114, seventh motor 115, and table slide mechanism 63. The configuration of table slide mechanism 63 is the same as the configuration in the second to fifth implementations described above, thus a description is omitted.

Pitch movable part 112 is linked to each link member 46b via a link shaft, and is rotatable in D5 direction (pitch direction) in FIG. 15. Pitch movable part 112 is driven to rotate in D5 direction by fifth motor 111 provided corresponding to the link shaft.

Pitch movable part 114 is linked to pitch movable part 112 via fourth joint 116, and is rotatable in D6 direction (roll direction) in FIG. 15. Roll movable part 114 is driven to rotate in D6 direction by sixth motor 113 provided corresponding to fourth joint 116.

Seventh motor 115 is provided between roll movable part 114 and table slide mechanism 63. Seventh motor 115 is a motor for rotating table 8 in a yaw direction (D7 direction) with respect to roll movable part 114.

It is to be noted that the configuration of each motor in the sixth implementation is the same as the configuration in the first implementation, thus a description is omitted. Similarly to the case of the first implementation, also in this implementation, each motor operates each movable part via a gear reducer.

As described above, robot arm 2e includes joints that are rotatable or slidably movable in D1 to D8 directions, and thus has eight degrees of freedom (7 rotational degrees of freedom and 1 linear degree of freedom). Also, referring to FIG. 15, wrist assembly 6e enables table 8 to be rotated in D5 direction (pitch direction), D6 direction (roll direction), D7 direction (yaw direction), and to be slidably moved in D8 direction. Thus, wrist assembly 6e has four degrees of freedom.

When thus configured robotic operation table 1e is used, similarly to the case of the first to fifth implementations described above, the table can be accurately moved to a predetermined target position, and thus the efficiency of the testing and treatment in medical practice can be significantly improved and the safety and movement efficiency can be enhanced.

[Operation of Robotic Operation Table]

The table can be moved between multiple positions within a movable range by robot arm 2e via a freely chosen route according to this implementation. Thus, the table can be moved to a testing device and others along the same path as in FIG. 5 to FIG. 7 which have been described in the first implementation. Specifically, robot arm 2e, which is stored in storage space S under table 8 and takes the first posture, is changed to take the second posture, thereby enabling table 8 to be moved from an operation position to a test position. Conversely, robot arm 2e in the second posture is changed to take the first posture, thereby enabling table 8 to be moved from a test position to an operation position.

[Effect]

As described above, with robotic operation table 1e according to the sixth implementation, similarly to the case of the first to fifth implementations, when table 8 is positioned at an operation position, robot arm 2e is stored in storage space S that is a space under table 8. Thus, it is possible to provide a robotic operation table that can sufficiently ensure the space around table 8 for placing a patient.

Also, by equipping with horizontal multi-articulated assembly 100 having three movable parts 102, 104, 106 as in robotic operation table 1e, it is possible to extend a movable range of table 8 in a horizontal plane while avoiding upsizing of robot arm 2e.

(Modification of Sixth Implementation)

For robotic operation table 1e according to sixth implementation, a description has been given by taking an example in which first movable part 102 included in robot arm 2e has an elongated shape as seen from above. However, the invention is not limited to this. Specifically, for instance, the first movable part may be formed in a circular shape as seen from above, as an example. In this case, for instance, the central portion of the circular first movable part is supported rotatably about a vertical axis by base 3, as an example.

(Seventh Implementation)

Figure 17A:
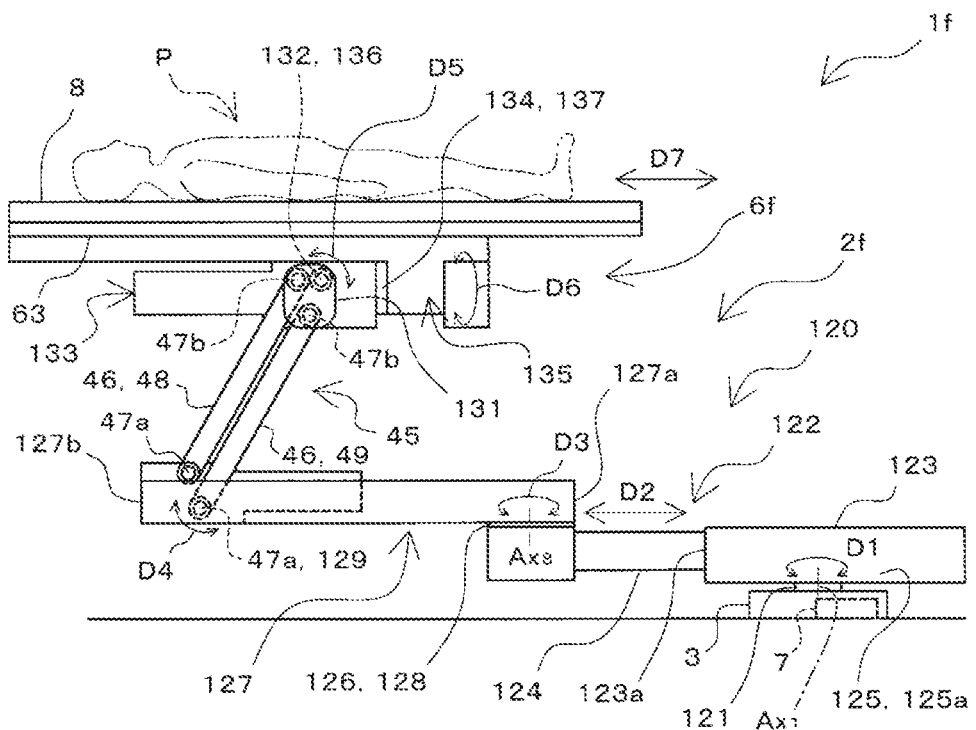
FIG. 17A is a side view of a robotic operation table according to a seventh implementation, and the view illustrates the robot arm in the second posture.
Figure 17B:
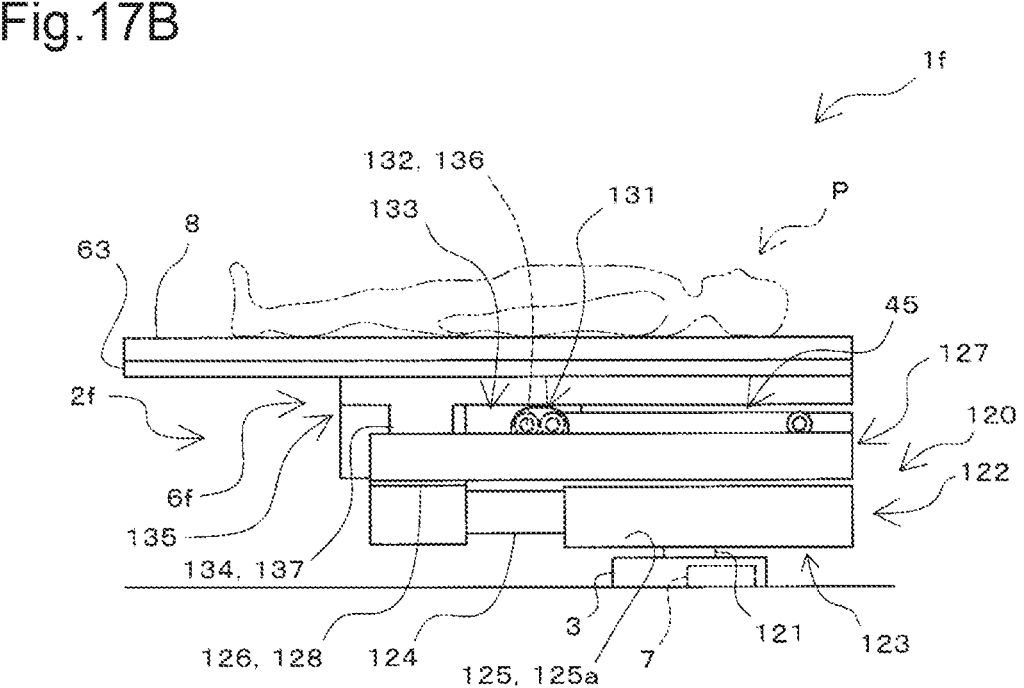
FIG. 17B is a side view of the robotic operation table according to the seventh implementation, and the view illustrates the robot arm in the first posture.

FIGS. 17A and 17B are each a side view of robotic operation table 1f according to a seventh implementation, FIG. 17A is a view of robot arm 2f in the second posture, and FIG. 17B is a view of robot arm 2f in the first posture. Robotic operation table 1f includes robot arm 2f, base 3, and table 8. In robotic operation table 1f, one end of robot arm 2f having multiple degrees (seven degrees of freedom in the case of the seventh implementation) of freedom is supported rotatably about a vertical axis by base 3, whereas the other end of robot arm 2f supports table 8 for placing a patient. The configuration of base 3 is the same as the configuration of base 3 in the first implementation, thus a description is omitted.

Robot arm 2f includes base-side movement assembly 120, parallel link mechanism 45, and wrist assembly 6f.

[Configuration of Base-Side Movement Assembly]

Base-side movement assembly 120 is for moving table 8 which is supported via parallel link mechanism 45 by base-side movement assembly 120. Base-side movement assembly 120 includes first motor 121, first movable part 122, third motor 126, and second movable part 127.

First movable part 122 is a section formed in a linear shape extending horizontally and configured to expand and contract its length. First movable part 122 includes linear movement mechanism 125 having base-side movable part 123, slide section 124, and second motor 125a.

Base-side movable part 123 is a section formed to extend horizontally, and a lower portion of one end side thereof is linked to base 3 so as to be rotatable about vertical axis $Ax_1$ (in D1 direction) with respect to base 3. Base-side movable part 123 has opening 123a which is open outwardly, in the other end portion in the longitudinal direction. Base-side movable part 123 is driven to rotate in D1 direction by first motor 121.

Slide section 124 is a section formed in a horizontally elongated rod-like shape, and one end portion thereof is stored in base-side movable part 123 with the longitudinal direction of slide section 124 being parallel to the longitudinal direction of base-side movable part 123. The other end portion of slide section 124 is extendable outwardly from opening 123a of base-side movable part 123, and is retractable into base-side movable part 123. In short, slide section 124 is provided to be slidably movable in the longitudinal direction of base-side movable part 123. Thus, the horizontal length of first movable part 122 expands and contracts.

Linear movement mechanism 125 is provided between base-side movable part 123 and slide section 124, and is configured to be capable of slidably moving slide section 124 with respect to base-side movable part 123. Linear movement mechanism 125 may be any mechanism as long as the mechanism is capable of slidably moving slide section 124 with respect to base-side movable part 123. As linear movement mechanism 125, for instance, a ball screw mechanism or a rack and pinion mechanism may be used as an example.

Second movable part 127 is a section formed in a linear shape extending horizontally. Second movable part 127 is coupled, at one end 127a, to the leading end of slide section 124 via first joint 128, and is rotatable about vertical axis $Ax_8$ (in D3 direction). Second movable part 127 is driven to rotate in D3 direction by third motor 126 provided corresponding to first joint 128.

Parallel link mechanism 45 is a link mechanism that links base-side movement assembly 120 and wrist assembly 6f together. Parallel link mechanism 45 is driven by fourth motor 129. Parallel link mechanism 45 has the same configuration as the configuration of parallel link mechanism 45 in the second implementation except that link targets are base-side movement assembly 120 and wrist assembly 6f, and thus a description is omitted.

Wrist assembly 6f has link plate 131, fifth motor 132, pitch movable part 133, sixth motor 134, roll movable part 135, and table slide mechanism 63. Among these, the configuration of table slide mechanism 63 is the same as the configuration of table slide mechanism 63 in the second implementation, thus a description is omitted.

Link plate 131 is a member that is formed in an approximately rectangular plate-like shape for linking parallel link mechanism 45 and pitch movable part 133 together. Link plate 131 is provided on both sides of pitch movable part 133 in the widthwise direction (direction parallel to the widthwise direction of table 8). Each link plate 131 is rotatably coupled to link members 46 via second link shaft 47b of parallel link mechanism 45, and is rotatably coupled to pitch movable part 133 via link shaft 136 provided between link plate 131 and pitch movable part 133. In other words, pitch movable part 133 is swingably coupled to parallel link mechanism 45 via link plate 131.

Pitch movable part 133 is coupled to link plate 131 via link shaft 136, and is rotatable about link shaft 136 (in D5 direction about the pitch axis) the extends horizontally. Pitch movable part 133 is driven to rotate about link shaft 136 by fifth motor 132 provided corresponding to link shaft 136.

Roll movable part 135 is a section attached to the lower side of table 8 via table slide mechanism 63. Roll movable part 135 is coupled to pitch movable part 133 via second joint 137, and is rotatable about the roll axis (in D6 direction) that extends in the front and back direction of table 8. Roll movable part 135 is driven to rotate in D6 direction by sixth motor 134 provided corresponding to second joint 137.

It is to be noted that the configuration of each motor in the seventh implementation is the same as the configuration in the first implementation, thus a description is omitted. Similarly to the case of the first implementation, also in this implementation, each motor operates each movable part via a gear reducer.

As described above, robot arm 2f includes joints that are rotatable or slidably movable in D1 to D7 directions, and thus has seven degrees of freedom (5 rotational degrees of freedom and 2 linear degrees of freedom). Referring to FIGS. 17A and 17B, wrist assembly 6f enables table 8 to be rotated in D5 direction (pitch direction) and D6 direction (roll direction), and to be slidably moved in D7 direction. Thus, wrist assembly 6f has three degrees of freedom.

It is to be noted that base-side movement assembly 120 according to this implementation is configured such that slide section 124 can be slidably moved in D2 direction with respect to base-side movable part 123. In other words, the base-side movement assembly has the function as a linear movement assembly. Also, in base-side movement assembly 120, first movable part 122 is provided rotatably about vertical axis $Ax_1$ with respect to base 3, and second movable part 127 is provided rotatably about vertical axis $Ax_8$. In other words, base-side movement assembly 120 also has the function as a horizontal multi-articulated assembly.

When thus configured robotic operation table 1f is used, similarly to the case of the first to sixth implementations described above, the table can be accurately moved to a predetermined target position, and thus the efficiency of the testing and treatment in medical practice can be significantly improved and the safety and movement efficiency can be enhanced.

[Operation of Robotic Operation Table]

The table can be moved between multiple positions within a movable range by robot arm 2f via a freely chosen route according to this implementation. Thus, the table can be moved to a testing device and others along the same path as in FIG. 5 to FIG. 7 which have been described in the first implementation. Specifically, robot arm 2f, which is stored in storage space S under table 8 and takes the first posture, is changed to take the second posture, thereby enabling table 8 to be moved from an operation position to a test position. Conversely, robot arm 2f in the second posture is changed to take the first posture, thereby enabling table 8 to be moved from the test position to the operation position.

[Effect]

As described above, with robotic operation table 1f according to the seventh implementation, similarly to the case of the first to sixth implementations, when table 8 is positioned at the first position, robot arm 2f is stored in storage space S that is a space under table 8. Thus, it is possible to provide a robotic operation table that can sufficiently ensure the space around table 8 for placing a patient.

Also, with robotic operation table 1f, by providing with base-side movement assembly 120 having functions as both a linear movement assembly and a horizontal multi-articulated assembly, it is possible to extend a movable range of table 8 in a horizontal plane while avoiding upsizing of robot arm 2f.

[Characteristics and Modifications in Common Between Implementations]

Hereinafter additional characteristics and modifications applicable to all of the first to seven implementations are described.

(1) Although each motor in the above-described implementations is preferably equipped with a position detector and an electromagnetic brake, without being limited to this, an electric motor not equipped with those may be used. In this case, a position detector and an electromagnetic brake may be provided externally of the electric motor. Although an electric motor has been illustrated as a drive source of each movable part in the above-described implementations, without being limited to this, an actuators other than an electric motor may be used.

(2) Although robotic operation table 1 not equipped with a table slide mechanism has been illustrated in the implementation, and robotic operation tables 1a to 1f equipped with a table slide mechanism have been illustrated in the second to seventh implementations, without being limited to this, table slide mechanism 63 may be or may not be provided in each implementation. However, it is possible to extend a horizontal movable range of table 8 by providing table slide mechanism 63 in each implementation. Although a description has been given by taking an example in which a servo motor is used for table slide mechanism 63 in the above-described implementations, without being limited to this, a table slide mechanism, which is manually slidable, may be adopted.

(3) The degrees of freedom of robot arms 2 to 2f may be different from what has been illustrated in each implementation.

(4) Although a description has been given in the above-described first and third implementations by taking an example in which a linear movement assembly and a wrist assembly are coupled by a joint rotatable about a horizontally extending axis as a center. However, without being limited to this, for instance, a linear movement assembly may support a movable member rotatable about a vertically extending axis, and the movable member may support the wrist assembly via a joint rotatable about a horizontally extending axis.

(5) Although the wrist assembly included in the robotic operation table according to the first to seventh implementations three rotational degrees of freedom, that is, a rotational degree of freedom for the roll direction, a rotational degree of freedom for the pitch direction, and a rotational degree of freedom for the yaw direction, without being limited to this, the wrist assembly may have three degrees of freedom including two out of the rotational degrees of freedom for roll, pitch, yaw, and one linear degree of freedom.

Figure 18:
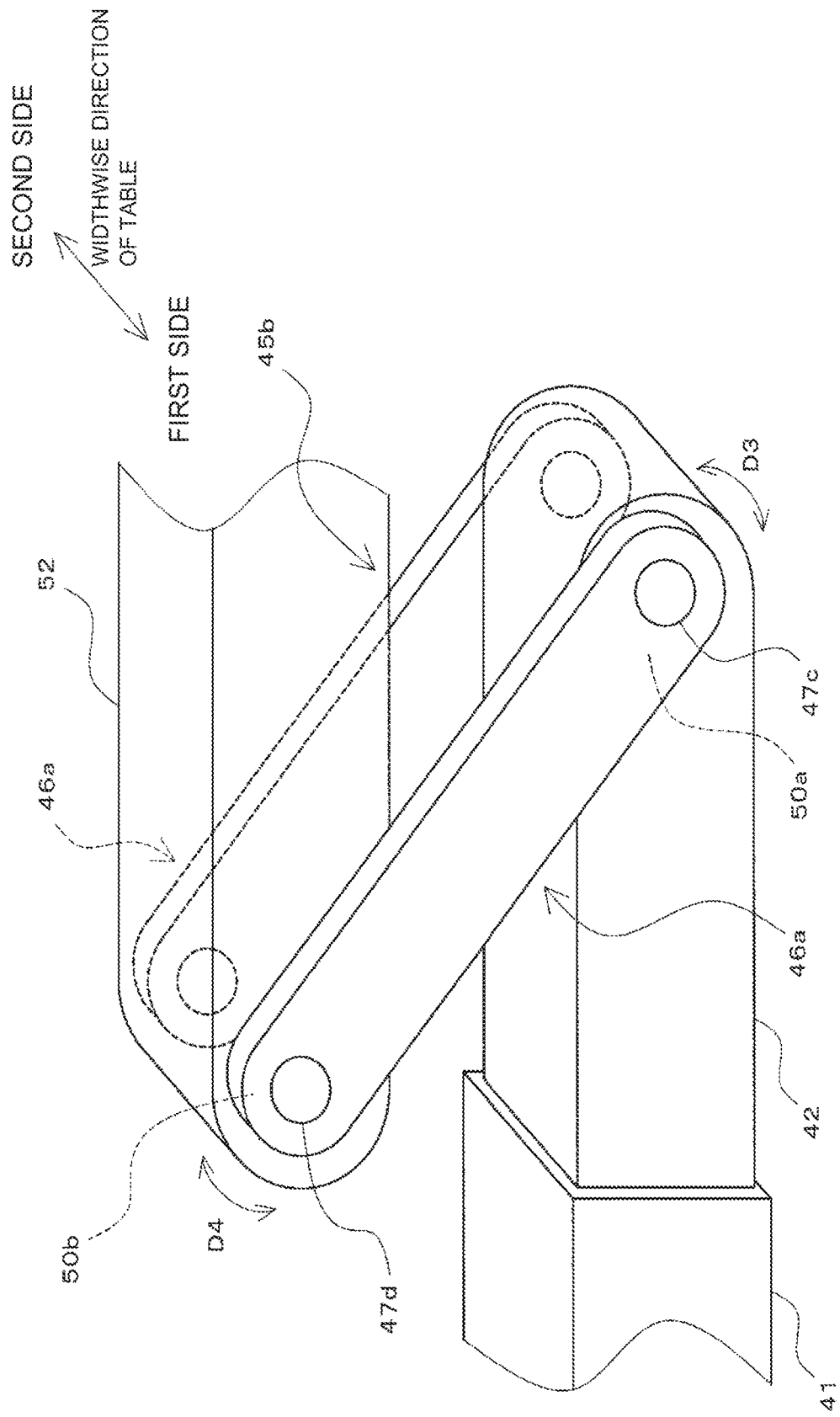
FIG. 18 is a schematic diagram illustrating the configuration of a parallel link mechanism according to another implementation.

(6) Although a description has been given by taking an example of parallel link mechanisms 45, 45a having four link members 46, 76 for the robotic operation table according to the second, fourth, and fifth implementations, without being limited to this, a parallel link mechanism having two link members may be formed. The parallel link mechanism having two link members is, for instance, as an example, two link members 46, 46 provided on one side of the table in the widthwise direction in FIG. 9 are replaced by one link member 46a, and two link members 46, 46 provided on the other side of the table in the widthwise direction in FIG. 9 are replaced by one link member 46a (see FIG. 18). In parallel link mechanism 45b, one end of each link member 46a is rotatably coupled to slide section 42 via first link shaft 47c, whereas the other end of each link member 46a is coupled to linear movement assembly-side movable part 52 via second link shaft 47d. Link member 46a is driven to rotate in D3 direction by motor 50a provided at a position corresponding to first link shaft 47c. Linear movement assembly-side movable part 52 is driven to rotate in D4 direction by motor 50b provided at a position corresponding to second link shaft 47d.

(7) The degrees of freedom of the wrist assembly in the above-described implementations are not limited to the number illustrated in each implementation, and may be at least two. Specifically, for instance, the wrist assembly may have two degrees of freedom for performing a roll operation and a pitch operation, and a yaw operation may be performed by a section other than the wrist assembly in the robot arm, as an example. Furthermore, although a description has been given by taking an example of a robot arm having a wrist assembly in the above-described implementations, the invention is not limited to this. Specifically, the invention is also applicable to a robot arm not having a wrist assembly. (8) Although movement of the table between the operation position and the test position has been explained in the above-described implementations, without being limited to this, for instance, when a catheter treatment is performed, the table of the robotic operation table in each implementation may move between a treatment position and a test position. In this case, at a treatment position, the robot arm takes the first posture and is stored in the storage space that is a space under the table, and thus the robot arm causes no interference with medical workers who perform the treatment.

[Application to Other Treatments]

The robotic operation table (the robotic-operation table with the above-mentioned common characteristics added depending on cases) presented in the first to seventh implementations is applicable to not only a hybrid operating room to which X-ray equipment used for angio test is introduced, but also a hybrid operating room to which a magnetic resonance imager (MRI) is introduced, for instance.

The technique disclosed by the aforementioned Patent Literature 2 and Patent Literature 3 uses a large robot arm for moving the table, thus the space around the operation table is narrow, which causes interference with medical workers when an operation is performed.

The above-described implementations are for coping with the above-mentioned problem, and provide a robotic operation table that can sufficiently ensure the space around the table for placing a patient without causing interference with medical workers when an operation is performed.

According to the above-described implementations, a patient placed on the table can be moved to a desired position by operating the robot arm as needed. In this manner, it is not necessary to manually move an operation table provided with a caster as in the technique described in Patent Literatures, thus problems such as entanglement between cables of the peripheral equipment caused by movement of the operation table, and a failure in applying the brake of the operation table are eliminated. That is, with this configuration, a patient placed on the table can be moved to a desired position safely.

Also, according to the above-described implementations, when the table is positioned at the first position which is a predetermined position, the robot arm is stored in storage space that is a space under the table. In other words, in this state, the robot arm does not horizontally protrude outwardly from the storage space.

Therefore, in the above-described implementations, it is possible to provide a robotic operation table that can sufficiently ensure the space around the table for placing a patient without causing interference with medical workers when an operation is performed.

In addition, in the above-described implementations, the table can be properly moved to the second position away from the base by changing the posture of the table from the first posture to the second posture. Also, with this configuration, the position and posture of the table can be flexibly adjusted by the robot arm having six degrees of freedom.

As described above, according to the implementations, it is possible to provide a robotic operation table that can sufficiently ensure the space around the table for placing a patient.

It should be noted that the embodiment disclosed above is illustrative in all respects and is not restrictive. The scope of the invention is presented not by the description of the embodiment described above, but by the claims, and moreover includes all modifications with equivalent meanings to and within the claims.

The invention claimed is:

1. An operation table comprising:
a table on which a patient is to be placed;
a base fixed on a floor; and
a robot arm comprising joints, a first end supported by the base, and a second end supporting the table, wherein
the robot arm takes a first posture in which the robot arm is stored in a storage space that is a space under the table when the table is positioned at a first position,
the robot arm moves the table to a second position which is away from the first position by taking a second posture in which at least part of the robot arm horizontally protrudes from the storage space,
the joints include a first joint rotatable about a first vertical axis, a second joint rotatable about a second vertical axis, a third joint rotatable about a first horizontal axis and a fourth joint rotatable about a second horizontal axis,
the robot arm comprises a wrist assembly that supports the table and includes the third joint,
the fourth joint supports the wrist assembly rotatably about the second horizontal axis,
the first position includes a descent position and an ascent position at which the table is lifted from the descent position, and
the robot arm moves the table between the descent position and the ascent position by at least one joint of the third and fourth joints.

2. The operation table according to claim 1, wherein
when the robot arm is in the first posture, a dimension of the robot arm in a direction parallel to a widthwise direction of the table is less than or equal to a width dimension of the table, and a dimension of the robot arm in a direction parallel to a lengthwise direction of the table is less than or equal to a length dimension of the table.

3. The operation table according to claim 1, wherein
the robot arm moves the table with at least six degrees of freedom.

4. An operation table comprising:
a table on which a patient is to be placed;
a base fixed on a floor; and
a robot arm comprising joints, a first end supported by the base, and a second end supporting the table, wherein
the robot arm takes a first posture in which the robot arm is stored in a storage space that is a space under the table when the table is positioned at a first position,
the robot arm moves the table to a second position which is away from the first position by taking a second posture in which at least part of the robot arm horizontally protrudes from the storage space,
the joints include a first joint rotatable about a first vertical axis, a second joint rotatable about a second vertical axis, a third joint rotatable about a first horizontal axis and a fourth joint rotatable about a second horizontal axis,
the robot arm comprises a horizontal multi-articulated assembly that causes translation movement of the table,
the horizontal multi-articulated assembly comprises the first joint rotatable about the first vertical axis and the second joint rotatable about the second vertical axis,
the robot arm comprises a wrist assembly that supports the table, and includes the third joint rotatable about the first horizontal axis, and
the horizontal multi-articulated assembly supports the wrist assembly via the fourth joint rotatable about the second horizontal axis.

5. The operation table according to claim 4, wherein
the horizontal multi-articulated assembly comprises:
a first movable part supported by the base via the first joint; and
a second movable part supported by the first movable part via the second joint.

6. The operation table according to claim 4, wherein
the horizontal multi-articulated assembly comprises:
a fifth joint rotatable about a third vertical axis;
a first movable part supported by the base via the first joint;
a second movable part supported by the first movable part via the second joint; and
a third movable part supported by the second movable part via the fifth joint.

7. The operation table according to claim 1, wherein
the robot arm comprises a table slide mechanism that moves the table with a linear degree of freedom, and the second end of the robot arm supports the table via the table slide mechanism.

8. The operation table according to claim 1, wherein
the robot arm causes the table to perform a roll operation, a pitch operation, and a yaw operation.

9. The operation table according to claim 1, wherein
the first position is an operation position, and the second position is a test position.

10. An operation table comprising:
a table on which a patient is to be placed;
a base fixed on a floor; and
a robot arm comprising joints, a first end supported by the base, and a second end supporting the table, wherein
the robot arm moves the table from a first position to a second position which is away from the first position,
the joints include a first joint rotatable about a first vertical axis, a second joint rotatable about a second vertical axis, a third joint rotatable about a first horizontal axis and a fourth joint rotatable about a second horizontal axis,
the robot arm comprises a wrist assembly that supports the table and includes the third joint,
the fourth joint supports the wrist assembly rotatably about the second horizontal axis,
the first position includes a descent position and an ascent position at which the table is lifted from the descent position, and
the robot arm moves the table between the descent position and the ascent position by at least one joint of the third and fourth joints.

11. The operation table according to claim 10, wherein
the robot arm comprises a horizontal multi-articulated assembly that causes translation movement of the table, and the horizontal multi-articulated assembly comprises the first joint rotatable about the first vertical axis and the second joint rotatable about the second vertical axis.

12. The operation table according to claim 10, wherein the robot arm comprises a table slide mechanism that moves the table with a linear degree of freedom, and the second end of the robot arm supports the table via the table slide mechanism.

13. The operation table according to claim 10, wherein the robot arm causes the table to perform a roll operation, a pitch operation, and a yaw operation.

14. The operation table according to claim 10, wherein the first position is an operation position, and the second position is a test position.

15. An operation table comprising:
a table on which a patient is to be placed;
a base fixed on a floor; and
a robot arm comprising joints, a first end supported by the base, and a second end supporting the table, wherein
the joints include a first joint rotatable about a first vertical axis, a second joint rotatable about a second vertical axis, a third joint rotatable about a first horizontal axis and a fourth joint rotatable about a second horizontal axis,
the robot arm comprises a horizontal multi-articulated assembly that causes translation movement of the table,
the horizontal multi-articulated assembly comprises the first joint rotatable about the first vertical axis and the second joint rotatable about the second vertical axis,
the robot arm comprises a wrist assembly that supports the table, and includes the third joint rotatable about the first horizontal axis, and
the horizontal multi-articulated assembly supports the wrist assembly via the fourth joint rotatable about the second horizontal axis.

16. The operation table according to claim 15, wherein the robot arm moves the table with at least six degrees of freedom.

17. The operation table according to claim 15, wherein the horizontal multi-articulated assembly comprises:
a first movable part supported by the base via the first joint; and
a second movable part supported by the first movable part via the second joint.

18. The operation table according to claim 15, wherein the horizontal multi-articulated assembly comprises:
a fifth joint rotatable about a third vertical axis;
a first movable part supported by the base via the first joint;
a second movable part supported by the first movable part via the second joint; and
a third movable part supported by the second movable part via the fifth joint.

19. The operation table according to claim 15, wherein the robot arm comprises a table slide mechanism that moves the table with a linear degree of freedom, and the second end of the robot arm supports the table via the table slide mechanism.

20. The operation table according to claim 15, wherein the robot arm causes the table to perform a roll operation, a pitch operation, and a yaw operation.

* * * * *